United States Patent [19]

Pfost et al.

[11] Patent Number: 5,369,566
[45] Date of Patent: Nov. 29, 1994

[54] USER PROGRAMMABLE CONTROL

[75] Inventors: Dale R. Pfost, Los Altos; Robert M. Coppock, Mountain View; Donald S. Murray, Sunnyvale; R. Fred Pfost, Los Altos; Brian Sanford, Cupertino, all of Calif.; Katherine L. Puckett, Cambridge, Mass.

[73] Assignee: Beckman Instruments, Inc., Fullerton, Calif.

[21] Appl. No.: 985,062

[22] Filed: Dec. 3, 1992

Related U.S. Application Data

[62] Division of Ser. No. 698,759, May 10, 1991, Pat. No. 5,206,568, which is a division of Ser. No. 844,374, Mar. 26, 1986, abandoned.

[51] Int. Cl.$^5$ .............................. G06F 15/46
[52] U.S. Cl. .................. 364/147; 364/140; 364/DIG. 2; 364/926.9; 364/949; 364/497; 395/375
[58] Field of Search ............... 364/140–147, 364/191–194, 496, 497, 502, 946.7, 926.9–926.93, 949–949.2, 262.4, 261–261.2; 395/375

[56] References Cited

U.S. PATENT DOCUMENTS

| | | | |
|---|---|---|---|
| 4,404,625 | 9/1983 | Saito et al. | 364/144 |
| 4,422,151 | 12/1983 | Gilson | 364/496 |
| 4,796,179 | 1/1989 | Lehman et al. | 364/191 |
| 4,953,075 | 8/1990 | Nau et al. | 364/140 |
| 4,965,742 | 10/1990 | Skeirik | 364/191 |

Primary Examiner—Jerry Smith
Assistant Examiner—Steven R. Garland
Attorney, Agent, or Firm—William H. May; P. R. Harder

[57] ABSTRACT

A method of programming a programmable controller in a manner by which a variety of menus, options, or questions seeking limited parameter answers are presented to the user; for example, setup parameters such as the type of labware, source and destination of reagent transfer etc. for conducting a particular biological and chemical assay experiments by an automated laboratory workstation. Software "templates" are used to focus the request for parameters from the user to tailor user needs to the laboratory workstation's capabilities. The software templates are designed to accommodate a wide variety of experimental setups in accordance with the setup parameters input by the user. By providing the parameters with the assistance of the templates, the user may program a complete set of instructions for conducting a biological or chemical assay. The instructions may include the time and method for undertaking the experiment. Further instructions may be given the laboratory workstation to conduct the later phases of experiments based upon earlier results of measurements.

5 Claims, 16 Drawing Sheets

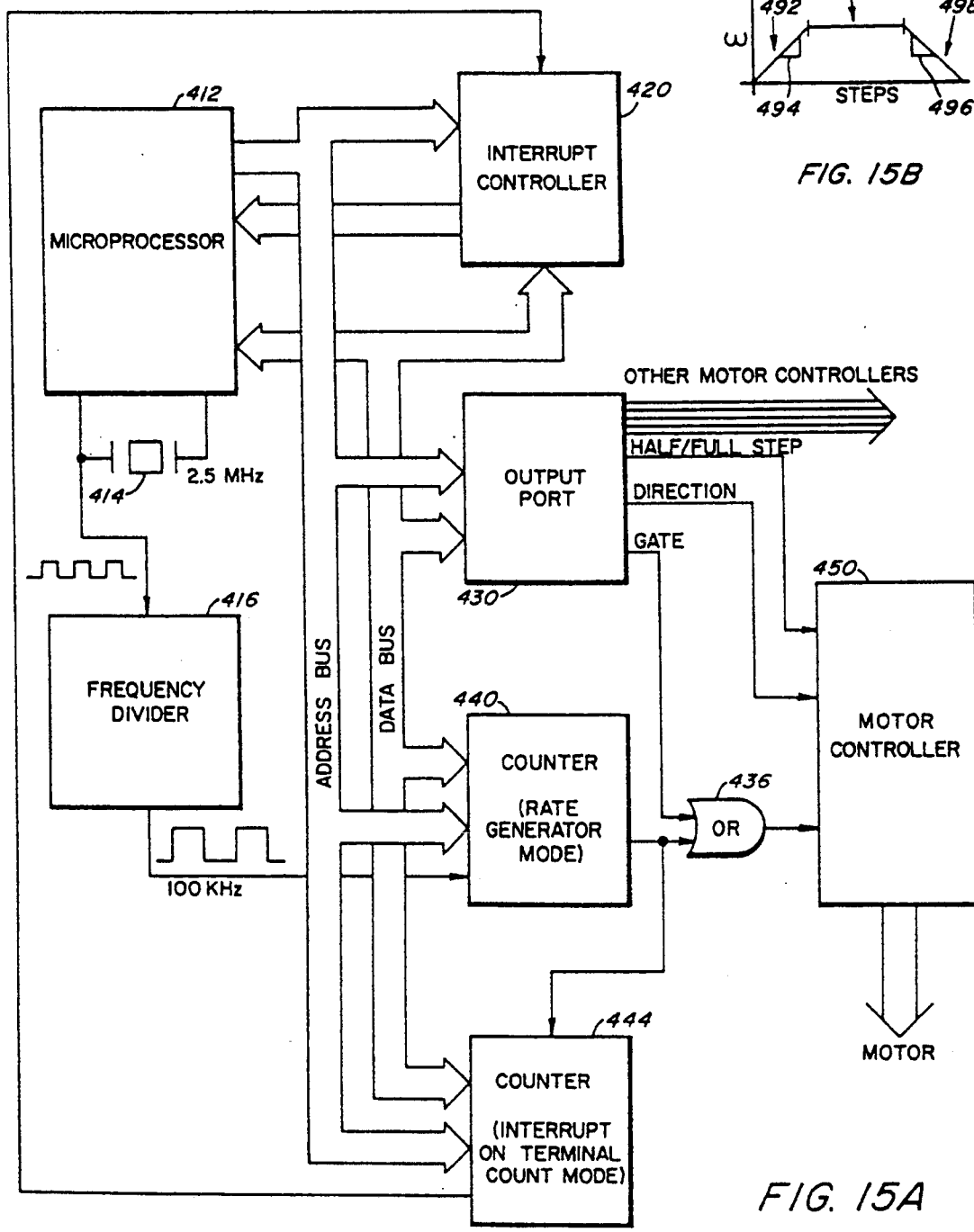
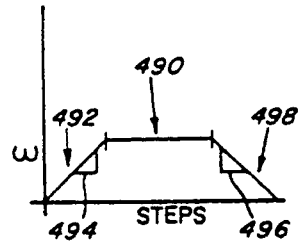
FIG. 15B
FIG. 15A

USER PROGRAMMABLE CONTROL

This is a divisional of application Ser. No. 7/698,759, filed May 10, 1991, now U.S. Pat. No. 5,206,568, which is a divisional of application Ser. No. 06/844,374, filed Mar. 26, 1986, now abandoned.

FIELD OF THE INVENTION

This invention relates to an analytical chemistry processing center and clinical and research laboratory workstation capable of performing the functions of several individual instruments, and, more particularly, to an automated laboratory work station useful in the performance of numerous chemical, biochemical, and biological assays and reactions.

BACKGROUND OF THE INVENTION

Modern research and clinical laboratory procedures include biological and chemical analysis of specimen substances that require extensive fluid manipulations. Many of the routine applications used for analysis are bioassays, immunoassays, viral assays, mitogen assays, serology, protein assays, lymphokine assays, and sample aliquoting. Experimental biological and clinical research include the use of photometric analysis of chemical reactions after the reactions have reached equilibrium or a fixed end point. Certain enzyme assays require a two-point or multi-point analysis embodying kinetic assays.

Standard fluid transfer and manipulative techniques include pipetting, diluting, dispensing, aspirating and plate washing. Conventional assays may be performed, in part, by rapid manipulation of manual pipettors or conducting assays which are piecemeal automated. Heretofore, the measurement portion of the assay, including determining optical or pH parameters, have been entirely manual or semi-automated. Common assays such as ELISA (enzyme linked immunoassay), vital, protein, and other biochemical studies and experimentation require liquid handling such as sample preparation, serial dilution, reagent addition and sample transfer to yield results. Bioassays and chemical experimentation which require making use of such liquid handling techniques, when performed manually, are replete with potential inaccuracies and error. It is difficult for a laboratory technician to accurately dispense the exact amount of liquid in each of 96 wells on a plurality of microtiter plates. The repetitious nature of liquid handling for experimentation inherently leads to mistakes which cannot always be detected. What has not heretofore been within the domain of biotechnology is a system which allows a bioassay to be carried out automatically from start to finish with little or no need for human intervention once the assay has begun.

Traditionally, the foregoing experimental, clinical, and other laboratory procedures require tedious step-by-step sample and control preparation which are then sequenced through a series of operations depending on the raw measurements, their analysis, and the nature of the chemical or biological investigation. As an example, the conventional experimental procedure for the production of monoclonal antibodies is essentially unchanged since first reported by Kohler and Milstein in Nature (Vol. 256, pp. 495-497-1975). Briefly, a mouse or rat is injected with an immunogen or antigen. The animal responds to the antigenic challenge by the production of antibodies. Mouse spleen cells from immunized animals are dissociated and fused with myeloma cells. Some of the resulting hybrids will include cells that produce only antibodies against one site on the challenge antigen.

Hybridoma selection and screening is a biotechnological procedure where samples of cell culture supernatants of cancerous myeloma cell hybridomas (a hybrid of a cancerous myeloma cell and a challenged lymphocyte) are tested to create, by manual pipetting, from sample volumes from growth plates to assay plates, a hybrid for the purpose of producing a single antibody with the immortal growth characteristics of the cancerous cell. The number of samples which require testing are commonly as great as 750. In order to select the desired hybrid cell, it is necessary to begin an experimental run starting with a single cell placed into hundreds of microtiter plate compartments or wells. Traditionally, the researcher manually analyzes each of the specimens after each clone has had a chance to grow and then determines whether the desired antibodies have been produced by use of optical spectroscopy in an immunoassay. Those cell colonies which are producing the antibody are actively grown for the rapid production of a monoclonal antibody, a desired product of the hybrid cells for the rapid production of a biochemically necessary substance. The cells are also recloned back to a single cell stage and grown for expansion for the production of additional antibodies.

The conventional hybridoma process as developed by Kohler and Milstein is based on the fusion of an antigen stimulated lympocyte (immunocyte) with a non-secreting myeloma cell. The myeloma cell which is cancerous confers immortality to the fusion partner, resulting an immortal, hybrid cell which secretes the antibody conferred by the lymphocyte. The antibody is specific to the stimulating or challenge antigen. Performing this process involves five major areas of work. They are cell fusion, cell feeding, screening and assaying of hybridomas, cloning and expansion. Each area of work can take up to a full eight-hour day requiring basic manual pipetting. Briefly, the hybridomas of a cell fusion are dispensed by manual pipetting to over 1000 wells of a plurality of 96-well tissue culture plates. The hybridomas are then nourished every three to five days by hand, aspirating the old media and replacing it with new cell culture media (this step results in about 2000 manipulations). Screening of the hybridomas is done to locate those hybrids which are secreting the antibody of choice. This process requires manually sampling up to 1000 wells by pipetting the cell culture out of each well and placing it into the wells of corresponding assay plates. An ELISA is performed on these plates whereby all reagents must be manually pipetted from reservoirs to the assay plate in proper physical order and time sequence. The results of the ELISA are determined by a conventional plate reader. These results must be correlated to the original growth plates for accurate selection and cloning. All data correlation has heretofore been done by the scientist through known computation techniques.

Selection of positive hybridomas is done based on the accurate calculated correlation of the results from the ELISA to the growth plates. Those wells which indicated a positive result are the cloned. This can be as much as 800 out of 1,000 hybrids. Cloning is done by distributing each hybridoma over an entire 96 well tissue culture plate. The cloned hybridomas are allowed to grow and are re-nourished as with the original plates.

All wells with hybridomas growing in them are again assayed for the production of antibody by the ELISA method. Data is obtained and correlated as before and those positive clones are expanded in numbers.

Each clone is manually pipetted from the 96 well tissue culture plate and transferred to the wells of a 24 well tissue culture and allowed to grow until an expanded cell number is reached. Subsequently, all clones are aliquoted (pipetted) manually into special freezing containers and frozen until needed.

Since the basic procedures of manual pipetting, data determination, and collection are common to all the applications described and since these applications are common to disciplines from biochemistry to virology, any system which can combine liquid handling, pipetting and plate reading will have broad applicability into many scientific disciplines which utilize these basic procedures.

As promising to biological research as the use of monoclonal antibodies appears to be (see, U.S. Pat. No. 4,376,110 issued Mar. 8, 1983 to Gary S. David et al., entitled "IMMUNOMETRIC ASSAYS USING MONOCLONAL ANTIBODIES"), conventionally, the practicality of using monoclonal antibodies has been heretofore limited. Compared with conventional antiserum (derived from polyclonal antibodies by known immunoassay techniques), hybridomas required a relatively high cost to prepare. Hybridoma production has been restricted by the limited variety of parental cells available for hybridization.

To produce large amounts of monoclonal antibodies, the hybridomas are grown as mass culture in vitro. Mass production of such antibodies requires improvement in the antibody concentration in the spent medium. Conventionally, the time required from the start of the in vivo immunization procedure to preliminary characterization of hybridomas is three months. The most labor intensive procedures are the maintenance of hybrids in culture and the assaying for antibody production.

It is the inevitable consequence of monoclonal antibody development that constant monitoring of the planned protocol of the experimental assay be conducted with a meticulous concern for detail and accuracy. As this biotechnological method for producing monoclonal antibodies is practiced, error resulting from tedious experimental repetition is likely. The conventional art simply lacked an instrument which could aid in reducing the time for practicing the ordered steps of protocol needed for antibody production, while, at the same time, increasing the relative purity of concentration of the isolated monoclonal antibodies without the introduction of increased error that normally accompanies stepped up production.

Other biological procedures and assays include investigative methods such as serial dilution which are conventionally performed by beginning with a plurality of separate samples of a substance at high (i.e. nearly 100%) concentration. These samples are then diluted to lower known (e.g. approximately 50%) strengths when mixed with diluent according to known methods of serial dilution, where successively increasing proportions of a diluent is added thereby obtaining a series of respectively decreasing concentrations of a sample. The various sample concentrations can then be assayed at a useful concentration to determine a particular property. For example, the sample might be a serum and the assay may employ a serial dilution which will demonstrate the relative concentration of the serum component to be measured which exhibits the greatest activity when reacted with a particular substance (such as a minimum inhibitory concentration (MIC) assay). U.S. Pat. No. 4,478,094, issued to Salomaa and assigned to Cetus Corporation of Emeryville, Calif., is an example of a liquid sample handling system which performs predetermined serial dilution by means of an automatic liquid transfer system operating within the framework of a fixed open loop system.

Conventionally, pipettors and micropipettors are operated manually by suction created through the user's mouth (an undesirable activity due to likely contamination) or with an automatic hand-operated pump or syringe. Such methods of pipetting can be long and tedious, susceptible to cross-contamination, as well as prone to measurement inaccuracies, and harmful to the scientist, where, for example, a given chemical or biological assay requires repetitious use of a pipettor for the introduction of a dissolved sample in hundreds of microtiter receptacle wells.

Another attempt at automating liquid sample handling is U.S. Pat. No. 4,422,151 issued to Gilson. The Gilson liquid handling apparatus discloses an open-loop system for fractional collection, sampling, dispensing, and diluting. The Gilson apparatus uses a microprocessor and three stepping motors to move a liquid handling tube suitable for dispensing or sampling in horizontal or vertical directions with respect to an array of test tubes or similar containers. No indication of the degree of precision and accuracy of liquid transfer is indicated in the disclosure of Gilson. The pattern of movement of the liquid handling tube may be selected according to a predetermined mode of operation which the operator desires. Once an operation is selected, it is fixed, and the liquid handling apparatus automatically carries out the instructions. The control means of the device described in the Gilson patent is used to selectively energize the drive motors for moving the carriage holding the liquid handling dispenser into positions corresponding to receptacle location positions and moving the holder device in three dimensions so that liquid may be transferred from one receptacle of a microtiter plate to another. Once the command is entered into the Gilson device, it is automatically carried out as instructed. Although such a device substantially reduces the need for manual effort in precisely measuring the pipetting or dispensing to be done for each of hundreds of receptacles, in particular bioassay or chemical assay, the Gilson device operates strictly in an open loop environment, performing fixed, predetermined liquid transfers.

Chemical and biological assays may be accomplished by the application of human judgment at every stage of the assay to control the course of experimentation. For example, the initial primary samples may be prepared manually or by an automated pipettor dilutor as disclosed in the Gilson and Salommaa patents. Conventionally, other instruments, such as an optical plate reader or a spectrophotometer, must be independently used to analyze a physical or chemical characteristic of each sample receptacle in the microtiter plate. After this tedious analysis is undertaken, the experimenter then selects to further analyze and subject to chemical or biological reactions only those sample plates which indicate a desired or optimum range characteristic. For example, in the hybridoma procedure as described hereinbefore, only those cell colonies which are producing monoclonal antibodies of the desired specificity are selected for further experimentation. Those cell colonies may be identified by spectrophotometric immunoassays which indicate an optimum optical density. Once the optimum samples are identified, only those samples are used in the latter stages of experimentation. Conventional manual methods of pipettor dilution and titration, as well as the devices disclosed in the Gilson and Salommaa patents, do not provide for any input by the operator to the direction of the assay on a real time basis once the experimentation has commenced. Being an open loop system, the conventional art is not able to execute the judgmental decisions preprogrammed by the researcher which respond to experimental data as the assay progresses.

U.S. Pat. Nos. 4,488,241 and 4,510,684 assigned to Zymark Corporation disclose a robot system with interchangeable hands and a module system; these patents are directed at a robot system for manipulating a series of discrete devices used in the field of analytical chemistry. These patents teach the use of a robotic arm to open, touch and manipulate discrete laboratory devices in an emulation of manual methods. These patents teach the use of a robot system to control these conventional laboratory instruments by their automatic manipulation; the techniques of the laboratory remain discrete and are not integrated into an intelligent and co-ordinated system.

Also, in the conventional art, even automated open loop pipettors did not provide for an integrated and flexible fluid dispensing system. Generally, the movable dispenser, as disclosed in the Gilson and Salomaa patents, has either a single nozzle or a multiple nozzle.

In the conventional art, such as the Gilson and Salomaa patents, the user had a limited menu and selection of programming available for liquid dispensing. What is needed is a flexible software operating system which will allow the researcher to tailor his use of the work station to the needs of his particular research project.

Additionally, the conventional art required the use of specialized motor controller integrated circuits dedicated to controlling robotic movement for discrete motor operation, such as the CY512 Stepper Controller IC chip, manufactured by. Cybernetic Micro Systems of San Gregorio, Calif. 94074. A flexible motor control system is needed which is adaptable for variable loads and which is programmable to avoid collisions and improper interaction between components of the robotic system.

Fulfilling the foregoing needs is the goal of the subject invention.

SUMMARY OF THE INVENTION

This invention relates to a multi-purpose laboratory work station which combines the operation of a number of existing discrete instruments, as well automating the performance of heretofore manual analytical chemistry and biological experimental assay procedures. The multi-purpose laboratory work station has a plurality of movable interactive components for the controlled dispensing, aspirating, and transferring of liquid from a first microtiter plate well or other fluid receptacle to a second microtiter plate well or other second fluid receptacle. The instrument of the invention also functions with test tubes, freezing vials, reservoirs and other wet chemistry containers. All fluid receptacles, such as microtiter plates, tip support plates, and troughs are supported in a movable support table attached to a laboratory work station base. The movable support table provides support for the microtiter plates and movement of the table is provided by a motor means, causing the table to reciprocally move in at least one axis.

Suspended above the table is a modular pod which is capable of reciprocal movement along the length of an elongated arm. The arm is attached at one end for movement up and down a vertically extending elevator tower rising from the base of the laboratory work station. The pod is capable of motion along the arm in at least a second axis which is perpendicular to the first axis of movement of the support table. The arm in turn moves up and down the elevator tower in a third direction which is perpendicular to both the first and second directions.

The pod may connect with and support a fluid dispensing, aspirating and transferring means. A displacement pump may be connected to the pod by fluid conduits to provide pipetting, dispensing, and aspirating capability. Interchangeable manipulative component modules containing the pump may be affixed to the pod and suspended above the movable table. The interchangeable modules may be uniquely identified by passive electronic means housed within each module. The interchangeable modules may have from one to eight or more nozzles in order to prepare samples for the receptacle wells of a microtiter plate or other fluid receptacle. The interchangeable modules may be designed to conform to a disposable pipettor tip. Some interchangeable modules may also be provided with a mechanism for ejecting disposable tips after completion of their use. The disposable pipettor tips may be sealed to the interchangeable manipulative modules by use of a friction fit.

The coordinated operation of the automated analytical processing center and workstation is directed by a microprocessor control means. The multi-purpose laboratory work station is capable of a wide variety of sample preparation and may be used for serial dilution, chemical and biological assays. The multi-purpose laboratory work station may, for example, be programmed for serial dilution sample preparation.

The multi-purpose laboratory work station additionally is provided with a transducer means housed within a module for performing spectrophotometric analysis. Optical fibers in the base of the laboratory work station provide an optical source beam which may be transmitted through transparent microtiter plates and the samples contained therein. The amount of optical radiation absorbed by the samples may be detected by the transducer means within an optical densitometer component. The pod may be connected to such an interchangeable optical densitometer module which houses a set of lenses, a rotatable filter means, and a transducer. This optical densitometer module is designed to mechanically interact with the same plunger mechanism which operates the fluid transport components, so that the same stepper motor which controls fluid dispensing of the fluid dispenser can be used to control optical filter selection. The source of light may be a chopper modulated light beam with an independent selection of source filters to accommodate a wide variety of optical experimentation, such as absorption or fluorometric data. This information is provided to the microprocessor by a specialized modulation technique and may form the basis of a closed loop system where the programmed instructions provided to the microprocessor require that the microprocessor control the operation of the laboratory work station, including the motor drive means and the pumping means, in accordance with experimental determinations made by the spectrophotometric transducer means. For example, if a biological assay is to be conducted, the laboratory work station will be instructed by the microprocessor to measure the optical density of a plurality of individual specimens on a microtiter plate. The microprocessor can be programmed to conduct subsequent testing, after a selected spectrometric measurement is determined, only on those samples which indicate an optical density within desired ranges. Such a closed loop system relies upon real time information provided by the transducer means and can automatically execute subsequent steps required in chemical and biological experimentation.

Interacting with the microprocessor is a remote user-controlled computer or other interactive device by which a variety of menus, options, or questions seeking limited parameter answers are presented to the user, each menu having a plurality of choices or instructions for conducting particular biological and chemical assay experiments. The operating system and software is designed to accommodate a wide variety of experimental techniques in accordance with a pre-programmed hierarchy of experimentation. A "template" program is used to focus the instructions for tailoring user need to the laboratory work station's capabilities. The user may program through a remote computer a complete set of instructions for conducting a biological or chemical assay. The instructions may include the time and method for undertaking the experimentation, as well as having the multi-purpose laboratory work station determine the chemical characteristics of the samples being tested by the transducer means. Further instructions may be given the laboratory work station to conduct the latter phases of experimentation based upon earlier results of the transducer measurements.

The automated workstation includes a programmable system for the control of a plurality of peripheral devices, such as stepper motors, to coordinate the flexible operation of the movable manipulated components. This control system includes a controller, such as a microprocessor, which transmits instructions to interface components which, in turn, communicate the intelligent instructions of the controller to the motor controller and motors. The interface components include ports to transmit data such as motor direction (clockwise-counterclockwise) and stepping mode (half-steps or full steps) to the motor. The transmission of operational data to the motor is timed by a frequency rate generator which powers the motors for a fixed step duration and a timing device which signals the microprocessor that the stepping cycle has been completed and the interface components are awaiting further microprocessor instructions.

Also included is a customized interchangeable module selecting mechanism which operates to accomplish (in the fluid dispense system) fluid dispense and aspiration, tip change and eject, and a change of removable manipulative module components by the operation of a single stepping motor driving a lead screw. A plunger body, riding along the extended lead screw, is made to manipulate fluid transport, tip eject, and also controls connection of the module component to the pod.

In an alternative embodiment, other transducer means could be, for example, a pH probe, temperature transducer or a video camera. In this manner, a fully integrated multi-purpose laboratory work station for the conduct of biological and chemical experimental assays is described.

BRIEF DESCRIPTION OF THE DRAWINGS

FIG. 15A is a schematic diagram of the hardware circuitry and computer architecture of the motor control system.

FIG. 15B is a graphic representation of a motor ramping cycle displayed graphically as angular velocity plotted as a function of time (measured in step numbers) as the cycle is practiced by the motor control system of this invention.

DETAILED DESCRIPTION OF THE PREFERRED EMBODIMENT

Figure 1:
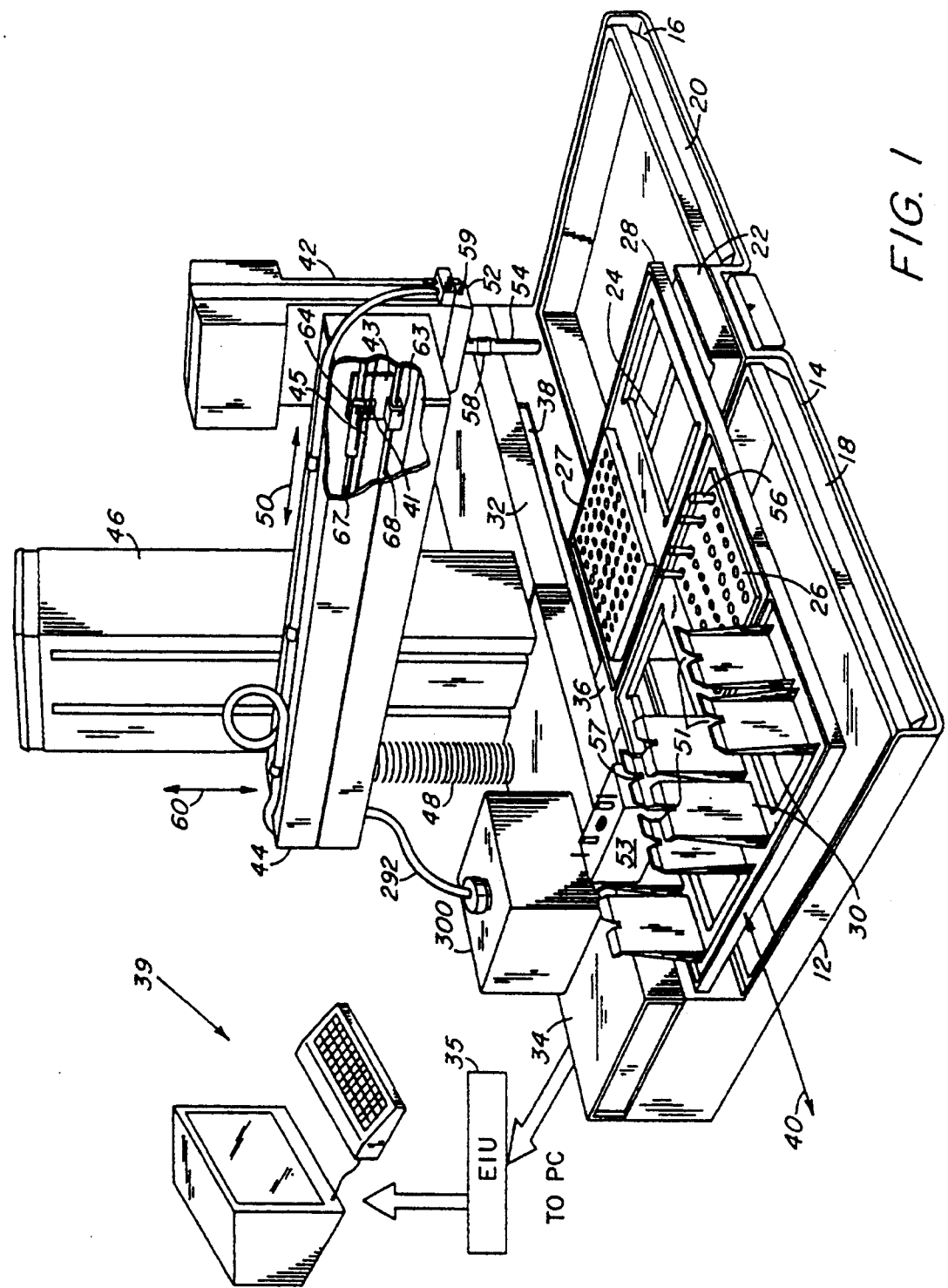
FIG. 1 is a perspective view of the multi-purpose laboratory work station of this invention.

Turning to FIG. 1, there is shown a multi-purpose analytical chemistry processing center and laboratory work station which is the subject of this invention. The work station has a fixed base 12 which may be seated to rest on the horizontal top of a laboratory work bench (not shown). In the preferred embodiment, the base 12 provides twin compartments 14 and 16, which define cavities for slidably housing a pair of drip pans 18 and 20. The twin compartments 14 and 16 each abut a central staging ridge 22. The central staging ridge 22 optionally houses, in the preferred embodiment, fiber optic illuminators 24 which direct optical signals in the form of light or other electromagnetic radiation upward from the base into the underside of microtiter plates or other receptacles such as 27, as plate 27 moves across the central ridge 22. The fiber optics 24 illuminates columns of the microtiter plate 27 one column at a time as the plate is moved by the table 28 reciprocally across the central ridge 22. Optical filters (not shown) may provide a wide or narrow band source illumination from the fiber optics 24 for photometric or spectrometric measurements.

The table 28 carries the microtiter plates 27 or other fluid receptacles, such as pipette tip tray 26, and the module holders 30 and is movable back and forth along the longitudinal wall 32 of the base housing 34. A stepper motor controls the movement of the table 28, the motor (not shown) being housed within housing 34 and connected to the table 28 by a bracket 36 protruding through slot 38. The table 28 moves reciprocally along axis 40 in a first direction. The table 28 is configured in the preferred embodiment to have a plurality of compartments in its frame, specifically six as shown in FIG. 1. In the drawing (FIG. 1), the two adjacent compartments are occupied by four pairs of the module holders like 30.

The module 53, when not in use, is seated between a pair of a module holders. The module holders are uniquely configured to receive interchangeable modules, such as 52 and 53. Module 53 is shown oriented for proper aligned mating with the pod 42 and seated within V-shaped notches of a pair of module holders. The V-shape notches 51 of the module holders 30 form a circular detent to receive the extended securement posts, such as 59 and 57. On each module 53, one of the securement posts may be of greater diameter than the other. The V-shaped notches 51 may be shaped so that for a given pair of holders like 30, one of the notches of one holder accommodates insertion of the greater diameter securement post of a module 53, and the other holder supporting the module 53 receives the smaller diameter post 57. In this manner, errors in module configuration on the table 28 may be avoided. The module holders 30 may be made from a resilient metal or organic polymer material. As module 53 was pushed into its resting position by downward movement of the pod 42 (driven by the arm drive motor 126 of FIG. 2), its module securement posts snapped into position at rest between the pair of module holders pressing axially along the module, since the holders are normally biased to stand upright on the table 28. As the pod 42 withdraws upward to release the module from the pod 42, the module 53 is grasped by the compressive action of the pair of module holders attempting to restore their normal upright position by pushing inward along the longitudinal axis of the module 53.

Immediately adjacent the compartments of table 28 are four additional compartments capable of holding microtiter trays 27 or tip racks 26, as well as fluid containing troughs or reservoirs, test tubes, or vials which may be used for multi-tip dispense and aspiration. The configuration of the table 28 is designed to accommodate removable trays for flexibility in the performance of experimental assays.

The pod mechanism 42 connects with an interchangeable module. 52 which houses a plunger and nozzle, which, when affixed to a pipette tip, is capable of transferring fluid from one well of the microtiter plate 27 to another well. The module 52 operates to automatically dispense and aspirate liquids from well to well, or reservoir to well, as programmed by the user. The pod 42 is attached to vertically movable arm 44, extending radially outward in a cantilever fashion, which is designed for sliding action along elevator tower 46. The pod 42 is movable along the length of the arm 44 parallel to longitudinal axis 50 of the arm which runs in a second direction. The pod 42 is affixed to an integral bracket plate 43 with a sliding collar 41 which rides along a lead screw 45 driven by a stepping motor (not shown) seated within the arm 44. The collar bearing means 63 and 64 slides along a parallel set of rails 67 and 68 to provide stability and prevent vibrations, assuring the pod moves reciprocally only along the axis of the arm 44. An electrical wire cable coil 48 is designed to accommodate the reciprocal movement of the arm 44 up and down the elevator tower 46 parallel to a third axis 60 for movement of the bridge 44 and pod assembly 42 in a third direction. Movement of the arm 44 up and down the elevator tower 46 is accomplished in a manner (not shown) similar to the described method of securement and movement of the pod 42 along the arm 44. In this manner, pod 42 can be accurately and automatically positioned for transferring fluid from at least one well of microtiter plate 27 to another well of that plate or to a well located in another microtiter plate housed within table 28. In the preferred embodiment, the stepper motor may operate at 200 pulse steps per revolution. Movement along the elevator proceeds at 0.0025 inches per pulse. The lead screw driven by the pod drive motor 124 (FIG. 2) allows linear movement of the pod at 0.005 inches per pulse. The table travels at 0.01 inches per pulse. The three dimensional transfer of fluid may be accomplished within a narrow range of accuracy. Precision volumetric pipetting is accomplished by pod plunger lead screw 242 (FIG. 7), which has a 0.375 inch pitch, allowing linear movement of the pod plunger as small as 0.00187 inches per pulse.

Connected interchangeably to the underside of the pod 42 is a module 52. As shown in the drawing, fluid transport module 52 has at least one nozzle 54. The nozzle 54 is adapted for receiving pipettor tips 56 seated within the tip tray 26 of the table 28 as shown in FIG. 1. In operation, the pod 42 is moved in position above a disposable pipette tip 56. When the pod 42 is in position directly above the pipettor tip 56, the arm 44 is lowered along elevator tower 46 thereby thrusting nozzle 54 to telescope into the disposable tip 56. After the pipettor tip 56 has been used and the operator wishes to dispose of the tip 56, pipettor tip ejector 58, located on the nozzle 54 of module 52, is activated downward along the nozzle 54 to remove the pipettor tip 56 from the nozzle 54. The pipettor tips 56 may be gathered at a single location within a tray 26 seated within a compartment of the table 28 where all the disposed pipettor tips 56 may be collected for sterilization and recycling or disposal. Alternatively, used tips may be placed in tray 26 in their original location. The module 52 hereinbefore described is exemplary of a fluid transport module. This description is but one example of an interchangeable module which may be affixed to the pod 42. The liquid transport modules, in the preferred embodiment, may have at least one nozzle 54, but may have up to eight nozzles, for servicing a multi-well microtiter plate.

The multi-tip module is generally configured to have sufficient nozzles to simultaneously fill a complete column of a (12×8) 96-well matrix format microtiter plate 27. Pipette dispensing and aspiration for all 8 wells of a column is driven by the movement of a single drive plunger 248 pressing against a volume plunger 250 (See, FIG. 7.). Disposable pipette tips 56 may be secured and removed from the multi-tip pipette module by the action of a single tip eject bar.

At those times during an experimental assay when fluid measurement is desired, the pod 42 may be moved over to the module holders 30 to retrieve an optical density module. The measurement module and optical detection system is described hereinafter in relation to FIGS. 3A, 3B, 3C, 3D, and 4. This module allows an experiment measurement of each well of the microtiter tray to determine optical density or fluoroscopic measurement of the specimen contained in the wells. The measurement information is relayed to the EIU 35, which may use this information to modify fluid transfers or other work station operations within the experiment according to user programming of the computer 39 at the commencement of the assay. In this manner, unique feedback driven progress of the experiment is achieved without the need for human intervention midstream of the assay.

Alternatively a pH measurement module could be implemented which has a pH probe to measure the pH of each specimen containing well. As with optical density measurement, the software could be programmed to make fluid transfers of specimen of only those samples within a desirable pH range during the course of experimentation. Another module could include a video camera which displays on the computer terminal a picture of each well for automatic imaging or analysis by the user. Again, fluid and specimen or other activities could be modified or originated as a result of analysis of the video imaging data.

Thus, any number of physical parameters, including optical and pH, could be measured and this measurement information supplied to the EIU 35 for further investigation by the user or to control progress of the experiment. For example, a user could program the workstation to create 24 wells of a specimen, transferring 48 hours later only those specimens which measure a pH of 8–10 to another microtiter plate. This could be accomplished by dispensing the specimen in the first 24 wells through use of a single tip, multi-tip or bulk dispense module, changing modules to a pH meter module, measuring acidity, changing modules, and transferring fluid, with fresh tips, to a new location.

If desired, multiple functions could be incorporated into the same module. By appropriate construction and arrangement the module may contain, for example, a single dispensing mechanism at one end thereof and a pH probe, optical density reader, or video camera at the other end.

For bulk dispensing functions, as an interchangeable module 52 configured in a bulk dispense mode (FIG. 12) is snapped into place below pod 42, the fluid tubing 292 is brought into operational engagement with the interchangeable component 52, so that the module 52 can serve to carry out the fluid dispensing, aspirating, and transferring functions as more fully described hereinafter of the bulk dispensing system (shown at FIG. 11A–C) encased within the pod 42.

Figure 2:
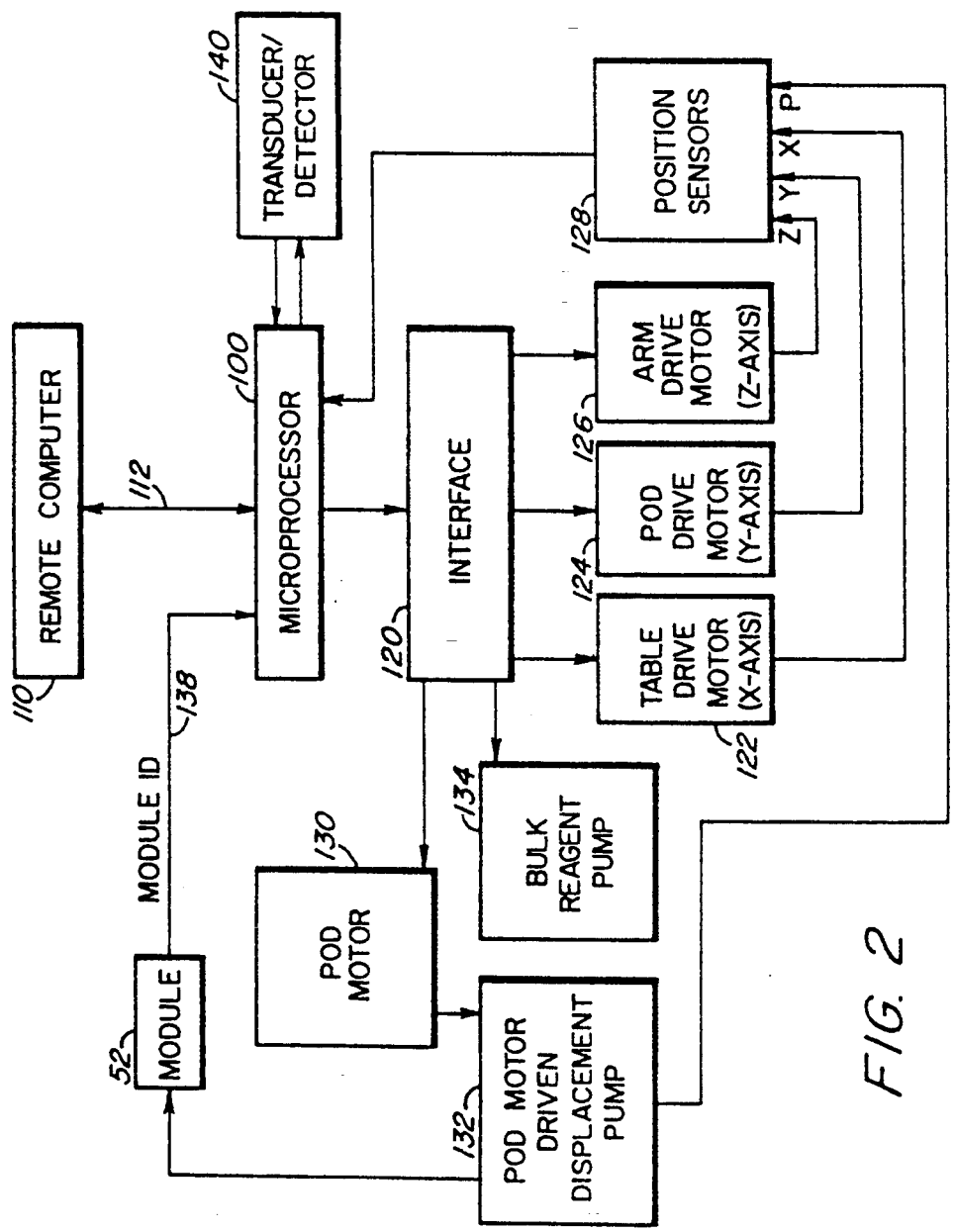
FIG. 2 is a schematic diagram of the operational hardware of the multi-purpose laboratory work station.

The electronic control of the movement, fluidic manipulations, and measurement mechanisms are controlled by an electronic interface unit (EIU) 35 (FIG. 1) which contains a microprocessor 100 (FIG. 2). Electronic interface unit 35 is shown as being interposed between the laboratory work station and a remote computer 39. The electronic interface unit may be preferably housed within the base 34 of the laboratory work station or alternatively be attached to the work station interposed between the work station and the computer 39. In the preferred embodiment, computer 39 has a "smart" terminal which may be, itself, a stand-alone computer, capable of being operated by a user by manipulation of the keyboard in accordance with well known higher level scientific and technical software languages. Alternatively, the EIU 35 containing the microprocessor is preferably stand alone, but may be built into the base housing.

In operation, the microprocessor 100 (FIG. 2) of the EIU 35 (FIG. 1) controls a number of stepper motors which drive the interactive components of the robotically controlled work station to function as instructed by the microprocessor. In the preferred embodiment, one stepper motor moves the table 28 along axis 40 in a first direction. Another stepper motor moves the pod 42 along the arm 44 in the second direction of axis 50. Yet a third stepper motor controls movement of the arm 44 along the length of elevator tower 46 in the third direction of axis 60. A fourth stepper motor controls a plunger body push rod for the single and multi-tip pipettor system contained in the pod 42; wherein, the pumping mechanism transfers fluids by dispensing and aspirating the fluids from one location on the table 28 to another, as well as tip ejection and module changing. In conjunction with the optical density module, this fourth motor controls filter selection and component change. A fifth motor drives a peristaltic pump in order to dispense bulk fluid from an external reagent container along tubing 292 through the pod 42 and nozzle 54 of the interchangeable module 52 for use in conducting an experimental assay.

Turning to FIG. 2, an operational systems block schematic diagram of the functions of the multi-purpose laboratory work station is presented. A microprocessor 100 is shown as the central system's control element. The user may program the microprocessor 100 through use of a remote computer 110 or other interface device. The remote computer is linked to the microprocessor along a bidirectional pathway 112 so that the microprocessor may display on the computer terminal the various steps of a planned experimental assay. The user may build his program for display on the computer screen, and during program execution, the status of an active assay may be displayed once the experiment begins.

The microprocessor controls movement of the interactive mobile components such as (FIG. 1) the table 28, the modular pod 42, and the arm 44, through the interface 120 (FIG. 2). This system interface 120 acts as a buffer between the microprocessor 100 and the motors which move the interactive components. (The clock used by the microprocessor is significantly faster than the stepper motor timing.) Each of the interactive components may be separately controlled by the microprocessor 100. The table drive motor 122 controls horizontal movement of the table 28 (FIG. 1). The pod drive motor 124 controls latitudinal movement across she plane of the microtiter plate 27, by controlling the position of the modular pod 42 along the arm 44 (FIG. 1). The arm drive motor 126 controls the movement of the arm 44 up and down the upright elevator tower 46. Each of these drive motors are linked with the interface 120. The microprocessor receives reference information by use of position sensors 128 (which may be an optical or mechanical sensor) which indicate when a secured mobile module crosses its axis origin or end point. In this manner, the microprocessor 100 can track the position of the mobile module and accurately position the module nozzle 54 or a module sensor with respect to any well or other receptacle on the tray carried by table 28.

Fluid transportation is controlled by the pod motor 130. This pod motor 130 is linked to the microprocessor 100. The fluid transport drive controls the pod motor driven displacement pump 132 as well as the motor for the bulk reagent pump 134. The pod motor driven displacement pump 132 controls the aspiration and dispensing of small quantities of liquid for the purpose of pipetting and diluting, as well as transferring liquid from one microtiter well to another. The motor for the bulk reagent pump 134 controls the dispensing of fluid from an external bulk reagent reservoir to a matrix of receptacle wells in the microtiter plates when the bulk dispense module of FIGS. 11A-C, described in detail hereinafter, is selected. Rapid dispensing may also be achieved by use of the multi-tip module aspirating fluid from a fluid receptacle trough positioned within one of the compartments of table 28.

The transducer/detector 140 provides a bidirectional link with the microprocessor 100 for real time physical characteristic data and information to the microprocessor. The microprocessor 100 in turn, according to a closed loop system, redirects control of the interface 120 and the fluid transport drive 130 in accordance with physical characteristic readings of transducer/detector 140. Additionally, the microprocessor 100 may instruct the transducer/detector 140, such as the optical densitometer module of FIG. 4A, to select from one of a plurality of optical filters in order that data be gathered at an experimentally desirable wavelength. Additionally, the microprocessor will instruct the transducer/detector to take readings of optical luminescence or fluorescence at a prescribed rate governed by the programmed instructions of the microprocessor. The multi-purpose laboratory work station is designed to therefore provide interactive communication of a bidirectional nature between the transducer detector 140 and the microprocessor 100.

As previously discussed, the multi-purpose laboratory work station provides for interchangeable modules 52 which are removable and versatile for the performance of a variety of functions. For example, a single tip nozzle connective module may be inserted into the pod 42, or an optical densitometer may be selected from the holder 30 to perform measurement functions. In order to distinguish the single nozzle from the optical module, the microprocessor 100 needs a system for module identification. Each module 52 is passively coded with a microprocessor readable code (stored by non-volatile passive means) which is provided to the microprocessor 100 by the module 52 along intelligence pathway 138. This module identification pathway 138 provides feedback to the microprocessor 110 to confirm that the microprocessor has selected use of a module which corresponds to the instruction provided by the operator. For example, if the operator wishes to aspirate liquid from a microtiter plate, the microprocessor must be sure that it is using a fluidic module rather than the transducer detection module. Also, if the instructions call for the dispensing of liquid in eight wells of a microtiter plate at a time, the multi-channel nozzle module must be used instead of the single head fluid nozzle module. The identification (I.D.) feedback pathway 138 is also useful to distinguish between, for example, using a module which measures pH vs. using the optical densitometer. Detailed operation of the module identification circuit is discussed later in the specification in conjunction with the description of FIG. 6.

Figure 3A:
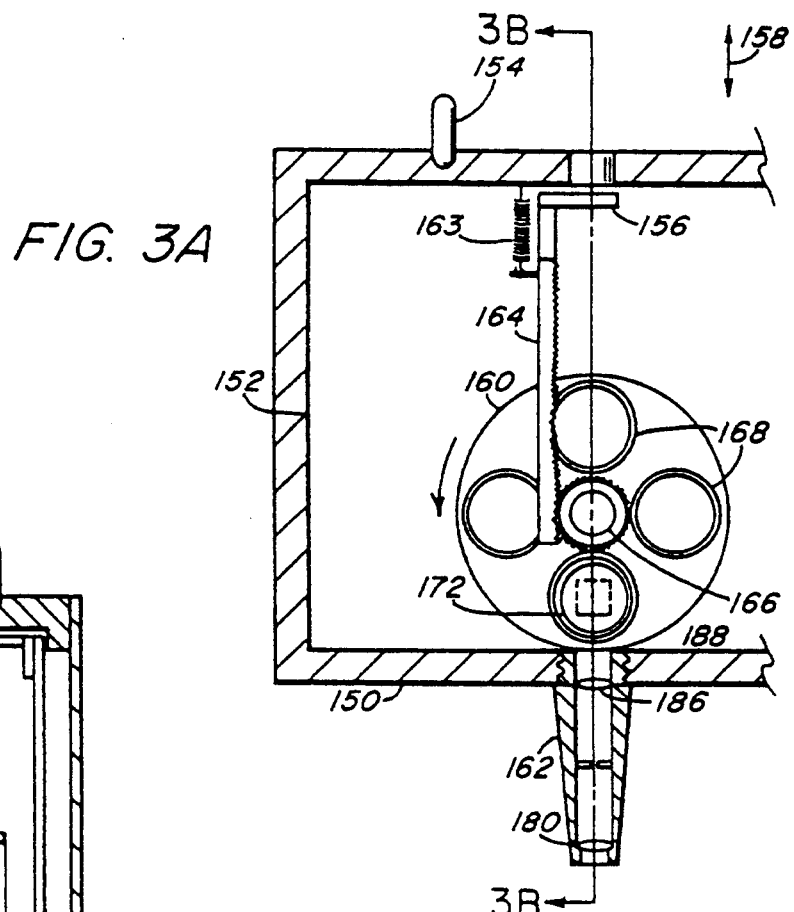
FIG. 3A is a laterally cross-sectional view of the optical densitometer module in the preferred embodiment.

Turning to FIG. 3A, an optical densitometer is shown to have an external casing 150 which surrounds an interior compartment 152 which is sealed to prevent the entry of extraneous light. Compartment 152 defines a dark environment for the proper processing of optical information derived from the microtiter plate. The optical densitometer module is secured by pin 154 to the pod 42 (FIG. 1). The plunger mechanism is driven by the pod motor 130 contained within the pod 42 as drive plunger 248 (See FIG. 9) drives against optical filter plunger 156 reciprocally along the direction shown by bidirectional arrow 158. As the plunger 156 moves towards the bottom side of the optical density module, a rack and pinion mechanism operates to rotate optical filter wheel 160. The rack and pinion mechanism is arranged such that a full stroke of the drive plunger 248 will rotate the wheel 160 270°. The mechanical stepper motor driven plunger 248 which is telescoped within pod 42 (not shown) and engages plunger 156 is the same plunger which drives the fluidic module 52. By driving the filter wheel 160 from its normal position in three 90° increments, any one of four filters may be placed in the optical path. When plunger 248 is retracted, a spring mechanism 163, normally biases the rack 164 upward to rotate the filter wheel 160 in a clockwise direction. Seated in the preferred embodiment of the optical filter wheel 160 are four different optical filters which may be used to select various narrow optical bandpass for the performance of specific bioassay experiments. Each of the optical filters 168 provide a differing wavelength for detection by the photodetector 170 which may be found at the bottom of housing 172.

Figure 3B:
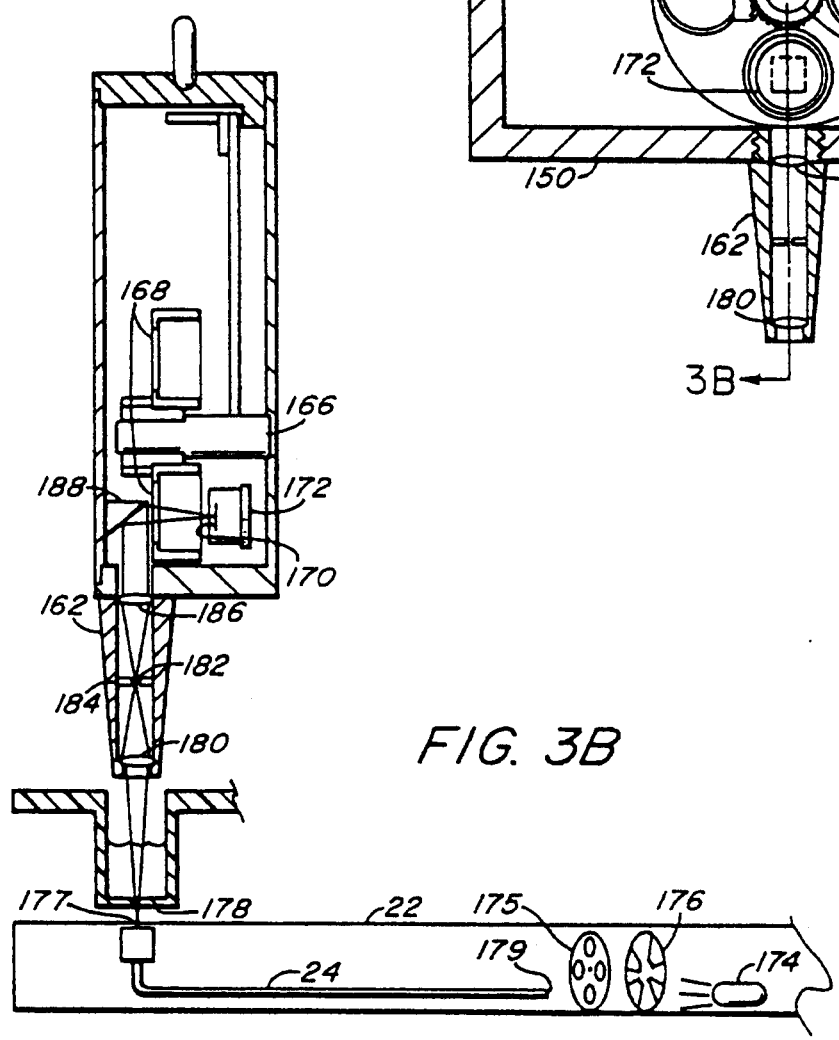
FIG. 3B is a cross-sectional view taken along lines 3B—3B of FIG. 3A showing an elevated cross-sectional view of the optical densitometer module and system.

With reference to FIG. 3B, light first passes through optical filter 168 before it reaches photodetector device 170. The filter wheel 160 rotates each time the plunger 156 moves to engage the rack and pinnion mechanism 164 tangential to the central shaft 166. In this manner, the rack and pinnion mechanism provides a plurality of filter choices for use in optical density readings.

With references to FIGS. 3A and 3B, a light source 174, an optional modulating chopper wheel 176, and fiber optics conduit 24 is housed within the central staging ridge 22 and the housing 34. For purposes of illustration, a single optical fiber 24 is shown, but in a preferred embodiment a series arrangement of at least eight optical fiber bundles run parallel down the center of the ridge 22 to provide a light source beneath each well of a row of eight wells in a microtiter plate. A filter wheel 175 allows the selection of bandpass selected optical wavelengths at the source, in order to perform measurements which require other than white light. Alternatively, the filter wheel 175 may have an opaque window to obscure the passage of light during times when no light is required. (The light must be "on" during normal operations to eliminate the "warm up" time associated with a non-energized cool lamp.)

The light source in the preferred embodiment may be a 42 watt tungsten-halogen projection lamp manufactured by Sylvania Company as Model No. EPT (a 42 watt-10.8 volt lamp). This light source has a built-in retro-reflector giving a spot a half inch in diameter and one and a half inches from the lamp mounting surface. The fiber optic bundle branches 24 each receive light at the forward end 179 of the fibers so that the rotating blade of the chopper 176 can easily cover the required illuminated area. Each branch bundle of fiber optics which illuminates one well 178 of a microtiter plate is about one millimeter in diameter. The light chopper 176 in the preferred embodiment has been built using a rotating disc with four black blades apertured 90° apart. This chopper may be driven by a six volt d.c. motor and preferably at about 8000 revolutions per minute (533 Hz). The fiber optics provides illumination to the transparent underside of a microtiter plate well 178.

Figure 3C:
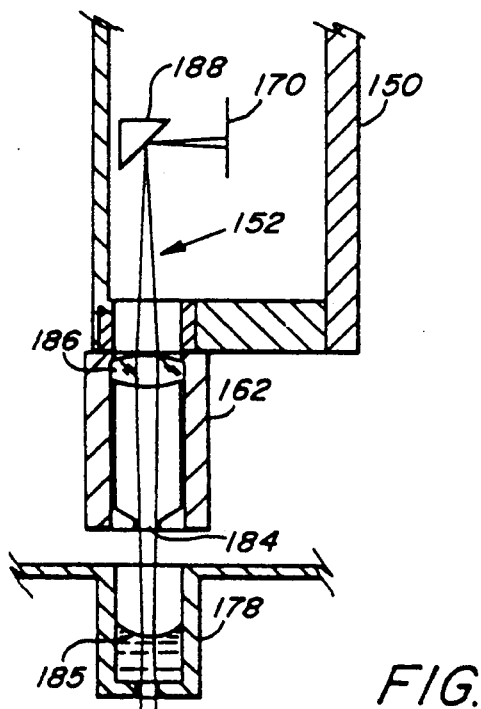
FIG. 3C is a laterally cross-sectional view of the optical measurement system showing light passing through a sample.
Figure 3C:
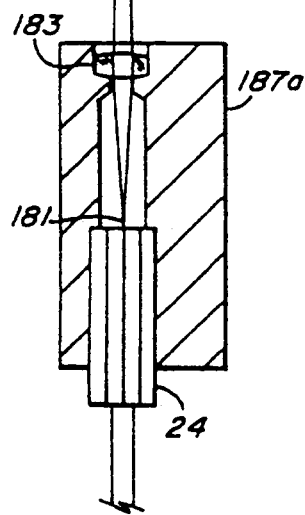

Details of the optics illumination system are shown in FIG. 3C. Light is transmitted outward from the end of the fiber optics bundle branch 24 through an optical aperture 181 for focusing through lens 183 which refocuses the light onto the base of microtiter well 178. The light is then transmitted through the fluid specimen forming a meniscus 185. The meniscus 185 of the fluid specimen acts as a negatively focused convex lens and tends to disperse exiting light as it passes from the meniscus 185 through the aperture 184. By securing lens 183 a fixed distance from the fiber optics bundle 24 within the fiber optics manifold section 187a (of manifold 187 of FIG. 3D), a thin pencil of light emerges from the meniscus 185 for transmission through aperture 184. In this manner, the entire light transmitted by the fiber optics bundle 24 falls onto the surface of the photosensor 170, eliminating any need for recalibration of the photosensor 170.

Figure 3D:
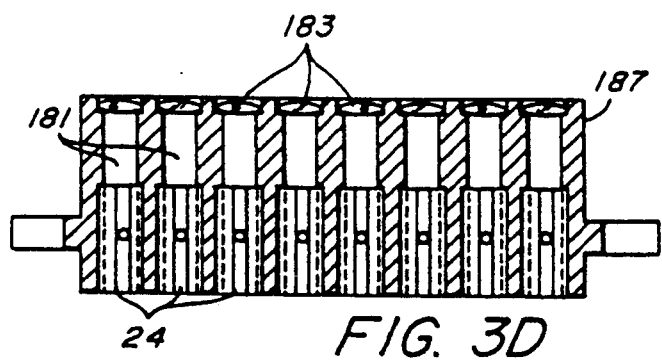
FIG. 3D is frontal cross-sectional view of the fiber optics manifold of FIG. 3C.

FIG. 3D shows a plurality of fiber optics branch bundles 24 and accompanying lenses 183 secured within manifold 187.

The light beam transmitted through the fiber optics 24 and through the microtiter well 178 is directed upward into the convex lens 180 of the optical densitometer (FIG. 3B). Lens 180 is contained within the lens holding tube 162, and the light from convex lens 180 is focused on the central aperture 182 of aperture plate 184. This light is then refocused and collimated by lens 186; the light is then transmitted into chamber 152 of the optical densitometer, and onto the aluminized side of triangular prism 188. Alternatively, as shown in FIG. 3C, a single lens 186 may focus light on the prism 188. Prism 188 acts to reflect the light which it receives from lens 186 onto the surface of electro-optical sensor 170. Light from the optical fiber bundle branch provides a thin pencil of light shining on the surface of the optical sensor 170. The pencil of light is of a cross-sectional area much smaller than the diameter of the sensor 170. In this manner, all the light which passes through the microtiter well 178 is reflected onto the sensor 170, even if the light beam is slightly deviated as it might be by a meniscus surface of the fluid 185. The information received by sensor 170 is processed and analyzed by an electronic circuit contained within housing 172.

The use of chopper 176 is optional with the choice of the user. The purpose of the chopper 176 is to provide a method of "synchronous detection" where a modulated signal is provided which differs from d.c. ambient light or any background a.c. fluorescent lighting that may be passing through the microtiter plate. Additionally, the modulation provided by chopper 176 may be used to eliminate the white noise inherent in the electronic circuitry which processes the signal received at the optical sensor 170. Finally, the chopper 176 acts to improve the signal-to-noise ratio by refining the light signal information provided by the optical fiber 24 through the microtiter well 178, as is well know in the conventional arts of synchronous detection using "lock-in" amplifiers.

Figure 4:
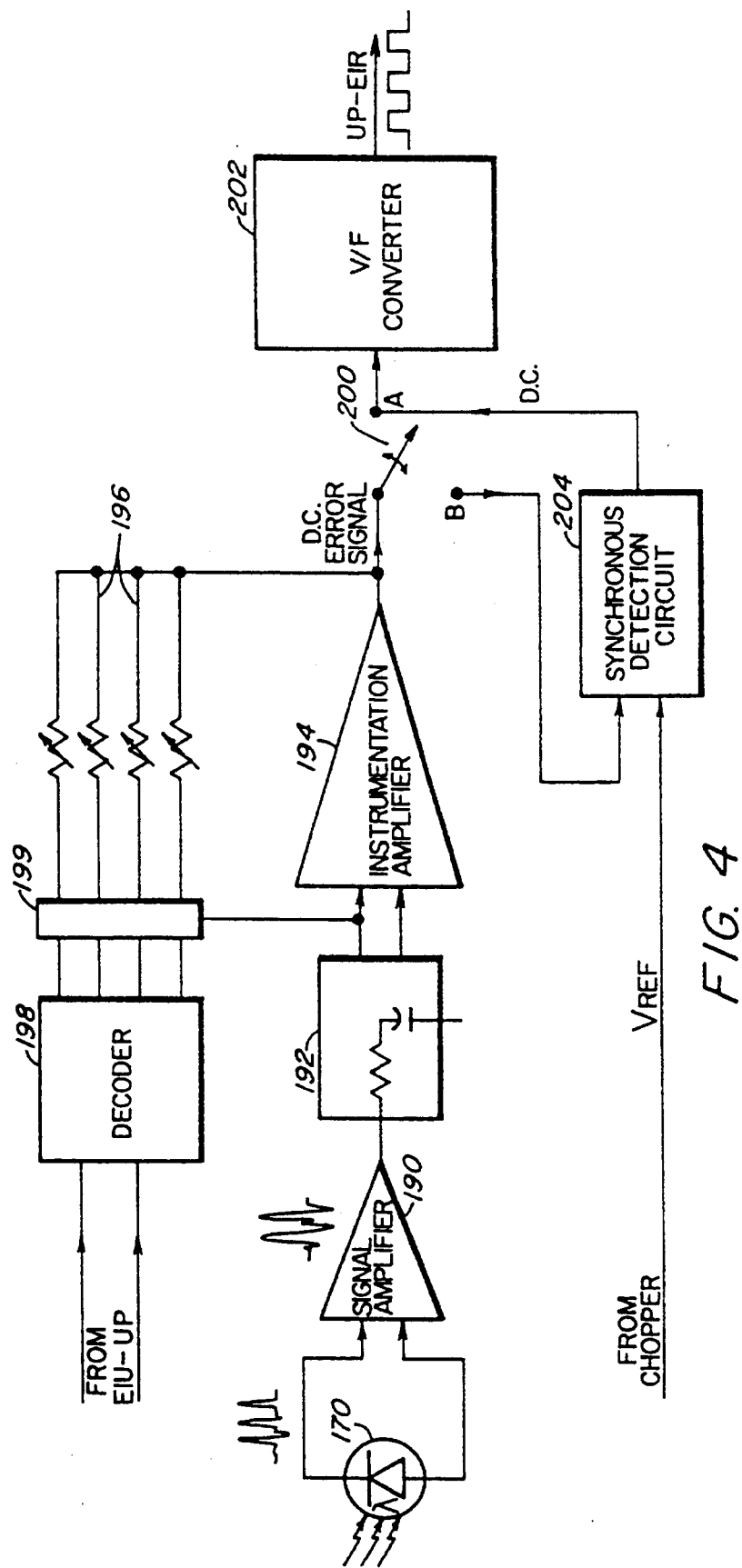
FIG. 4 is a detailed schematic drawing of the electronic circuitry of the optical densitometer detection system of the invention.

Turning now to FIG. 4, the optical sensor 170 of the optical densitometer of FIGS. 3A and 3B responds to light by producing a signal which is input to a signal amplifier 190. The output of amplifier 190 produces a higher level signal which corresponds peak to peak with the weak input provided to the amplifier 190 by the optical sensor 170. (The optical sensor 170, a photodiode in the preferred embodiment, together with signal amplifier 190, is available as an integral package as Part No. S1406-04 from Hamanatsu Electronic Company of Japan. The packaged operational amplifier acts as a preamplifier to the optical sensor output signal.) The output signal of the amplifier 190 is then passed through a low pass filter 192, which in the preferred embodiment may be a "T" or bridge-formation RC low pass filter. The signal which passes through the low pass filter 192 has a cut-off frequency in, the preferred embodiment of no more than 1,000 Hz. This signal is then passed to an instrumentation amplifier 194 which produces a signal at its output which is proportional to the signal presented to its input by the amplifier 190. The output of amplifier 194 is generally a d.c. signal. (A preferred embodiment of the instrumentation amplifier is Model INA101AN Instrumentation Amplifier manufactured by Burr-Brown Corporation of Tucson, Ariz.) The amplifier has an externally provided gain control which in the preferred embodiment of this invention is shown as a plurality of feedback resistors 196. The gain of the instrumentation amplifier 196 needs to be adjusted dependent upon the particular optical filter selected by the user as described in FIGS. 3A and 3B. Since a single optical sensor 170 is used to detect light which may be filtered through any one of the optical filters selected, the signal output of that sensor 170 will vary depending on the optical filter used. It is therefore necessary to adjust the gain of the amplifier 196 in order that the full dynamic range of the optical sensor 170 is utilized in detecting optical information from the light which passes through the microtiter well sample.

In order to control the gain of instrumentation amplifier 194, the preferred embodiment allows the microprocessor of the electronic interface unit 35 (FIG. 1) to select a gain which corresponds to a particular optical filter selected by the user. Thus, if four different optical filters are provided as shown in FIGS. 3A and 3B, then one of four resistors 196 must be selected to particularly adjust the gain of the instrumentation amplifier to accommodate the signal processing of optical information from the particular monochromatic filtered light information. In the preferred embodiment, a Texas Instrument Model SN74156N "Two-to-Four" Decoder is used to select one of four resistors for adjusting the gain of instrumentation amplifier 194. Interposed between the decoder 198 and the resistors 196 may be a plurality of mechanical Reed switches 199 having a low impedance for assisting the output of decoder 198 in properly selecting the desired gain resistance 196 for the instrumentation amplifier 194. One of a plurality of the resistors 196 is selected by the decoder 198 which closes one of the reed switches contained within component 199, causing the instrumentation amplifier 194 to select one of a plurality of gains, such that signals which are weak on input to the instrumentation amplifier 194 will be of equal output strength at switch 200 to drive V/F (voltage to frequency) converter 202. The output signal of instrumentation amplifier 194 is then provided to the single pole, double throw switch 200. When the switch 200 is closed to connect with terminal A of instrumentation amplifier 194, the output signal is provided directly to the V/F converter 202. Alternatively, when a chopper 176 is used at the light source, as discussed in FIGS. 3A and 3B, the output of instrumentation amplifier 194 is connected to contact point B for input into a synchronous detection circuit 204 for further processing. Also input to the synchronous detection circuit 204 is a reference signal ($V_{ref}$) from the light chopper 176 which monitors the frequency at which the chopper is rotating. The synchronous detection circuit 204 operates in accordance with known lock-in amplifier techniques. Lock-in amplifiers are widely used for measuring low level signals. This control reference voltage from the chopper and the amplifier signal from the optical sensor are heterodyned and demodulated within the synchronous detection circuit 204 and passed internally through a low pass filter (not shown) located within circuit 204. The output of the synchronous detection circuit 204 may be a fully rectified synchronous detection signal which is input to the voltage-to-frequency converter 202.

The voltage-to-frequency converter 202 in the preferred embodiment may be a Model No. VFC100AG manufactured by Burr-Brown of Tucson, Ariz. In the preferred embodiment, the voltage-to-frequency converter 202 is crystal controlled by an oscillator running at 2.5 MHz frequency. This 2.5 MHz frequency signal is frequency modulated by the analog output signal from the detection circuit 204 or the instrumentation amplifier 194, depending upon the selection of analog signals presented to switch 200. The output signal from the voltage-to-frequency converter may be a 0.25 to 1.2 MHz signal which is transferred to the electronic interface unit microprocessor 100 (FIG. 2) for signal range interpretation. The voltage-to-frequency converter 202 translates the analog optical density information signal to a modulated carrier signal which is capable of interpretation by the microprocessor 100 of the electronic interface unit 35. In this manner, a highly sensitive and wide ranging noise-free light detection system without spikes or other interference is provided through the use of a frequency discriminator. If no chopper 176 (FIG. 3B) is used, then the output signal from the instrumentation amplifier 194 is directly conveyed to the voltage-to-frequency converter where it is translated to a modulated carrier signal for interpretation by the microprocessor of the electronic interface unit. A conventional voltage-to-frequency converter, not running according to a fixed external clock, would have a true frequency modulated carrier signal.

In this manner, a microtiter plate like 27 having 96 wells may be read providing rapid optical density information to the microprocessor for each of the 96 microtiter wells.

Figure 5:
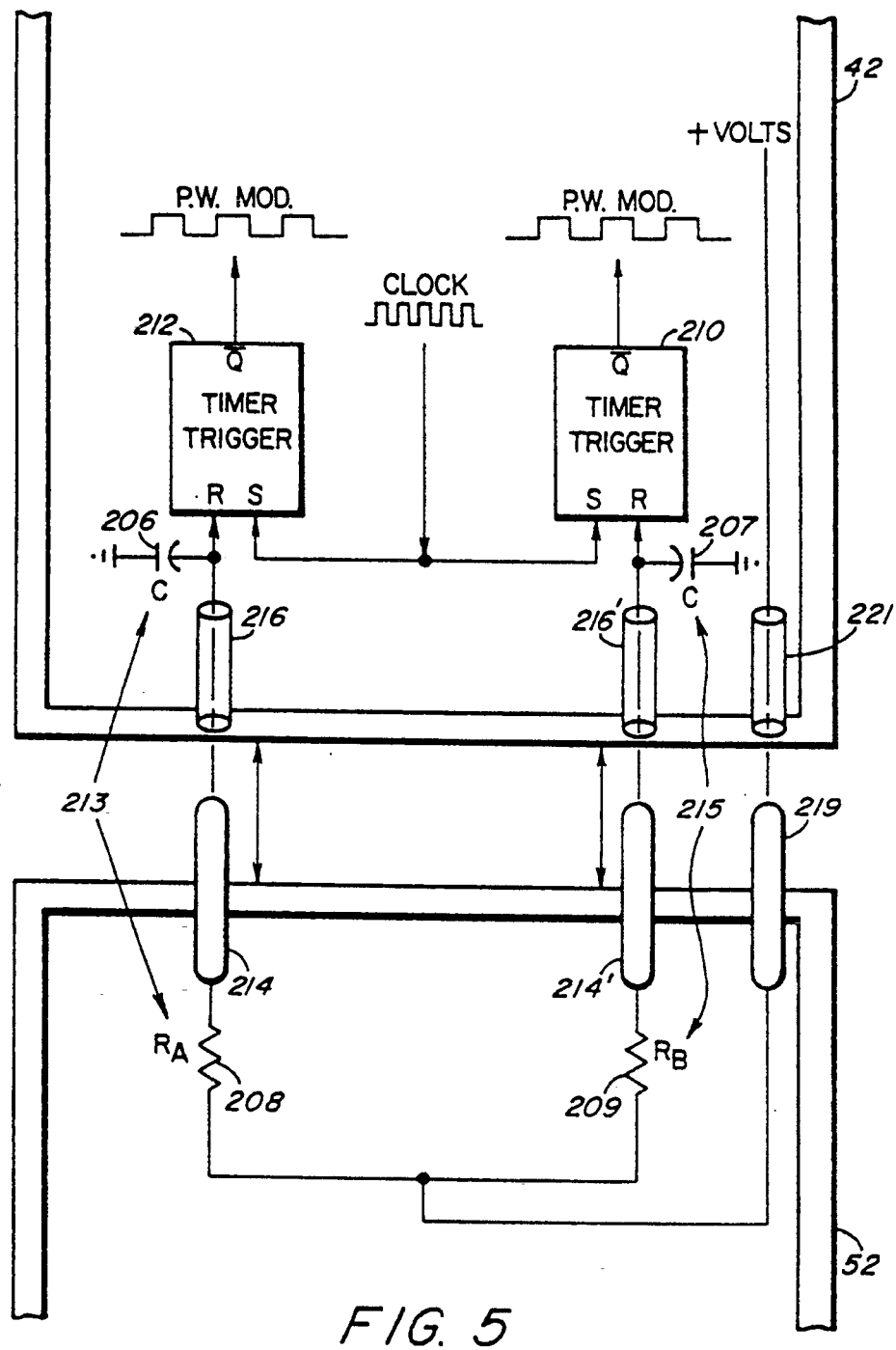
FIG. 5 is a cross-sectional view showing the interconnection and schematic operation of the module identification circuitry.

With reference to FIG. 5, there is shown an identification circuitry arrangement whereby the microprocessor has the ability to identify and distinguish a particular module 52 so that the microprocessor is aware that the proper module is being selected. In FIG. 1 of the preferred embodiment, each interchangeable module 52 is stored in a particular module holder 30. This storage location information is, in turn, indexed in the microprocessor so that when the table 28 and translational pod 42 are moved to position the pod over a particular holder 30 location, the microprocessor can be assured, after it engages the module, that it is engaging the proper interchangeable module selected by the operator. This system needs verification through an electronic module identification means which is provided as shown in FIG. 5.

In the preferred embodiment a monolithic integrated circuit such as a dual timing circuit manufactured as Model No. MC3456 by Motorola Corporation may be contained in the EIU 35 or within the housing of pod 42, as shown at 210 and 212. In the preferred embodiment, the heart of the dual timing circuit may be an RS reset flip-flop timing circuit which is subject to external synchronized clock control through the set ("S") input as shown at 210 and 212. The output of the timer circuit is a pulse width modulated signal, each pulse width modulated signal communicated at the output of circuits 210 and 212 as indicated by $\overline{Q}$. The width of the pulse width modulated signal is controlled by the time constant of the external RC circuits 213 and 215 shown at the respective reset "R" inputs of timing circuits 210 and 212. Positioned within each module 52 are, in the preferred embodiment, two separate resistors ($R_A$) 208 and ($R_B$) 209. In the preferred embodiment, capacitors 206 and 207 combine, respectively, with resistors 208 and 209 to form, respectively, two RC networks 213 and 215, when pins 214 and 214' connect with plugs 216 and 216' and power is provided the circuit by the connection of pin 219 into plug 221. In the preferred embodiment, the capacitance of the RC network remains fixed while the resistance of each network is varied to identify each module. Varying the time constant of the RC network varies the pulse width (P.W.) modulated signal output from each timer 210 and 212. It is generally understood that a plurality of identifying resistors and resistances may be used in conjunction with the RC circuits of the dual timers. Then the interchangeable module 52 is plugged into the underside of pod 42, conductive pins 214 plug into female pin-receiving contacts 216 so that the external RC time constant for each of the dual timers is adjusted in accordance to the resistance ratings set by resistors 208 and 209, respectively, contained within the module 52. Each of these resistors 208 and 209, in combination with the capacitors, control and determine the pulse width of the output signal which is sent to the microprocessor of the electronic interface unit for further analysis.

In this manner, a two-pin (214 and 214') information channel may be used to identify a multitude of different modules or instruments. In the preferred embodiment the resistors 208 and 209 may be one of four resistances, each resistance set apart by a decade of rating, such as 10, 100, and 1,000 ohm ratings. For the preferred embodiment, each dual timer circuit 210 and 212 can select between four different signals produced by four different resistors 208 and 209. In this manner one of 16 different modules may be selected since the number of combinations (C) is computed by the formula $C=2^n$, where "n" is the number of resistance rating choices, namely four. In this case, two information pins means $2^4$ combinations or 16. Alternatively, but not shown, the resistors 208 and 209 could each respectively be plugged into voltage comparators or Wheatstone bridge circuits for providing a threshold triggering signal for informational analysis by the microprocessor.

In summary, a unique but simple passive and nonvolatile module identification circuitry enables the electronic interface unit 35 and microprocessor 100 to distinguish and verify that the module connected to the pod 42 is the one selected by the operator for use in this segment of the chemical assay. The identification circuitry has a set of digital output components, such as timers 210 and 212, which produce signal readable by the microprocessor 100. The duration or coding of these digital signals may be controlled by passive components such as the resistor and capacitor which makes up the external RC networks which set the time constants for the timers. What is unique about the module identification circuitry of this invention is that the "intelligence" or information needed to identify a module need not be stored in a memory circuit but may be a function of the rating characteristics of one of the passive components.

Figure 6:
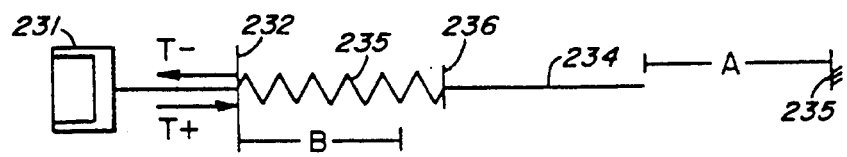
FIG. 6 is a schematic representation of the automated module change, tip ejection, and fluid aspirating and dispensing mechanism.
Figure 7:
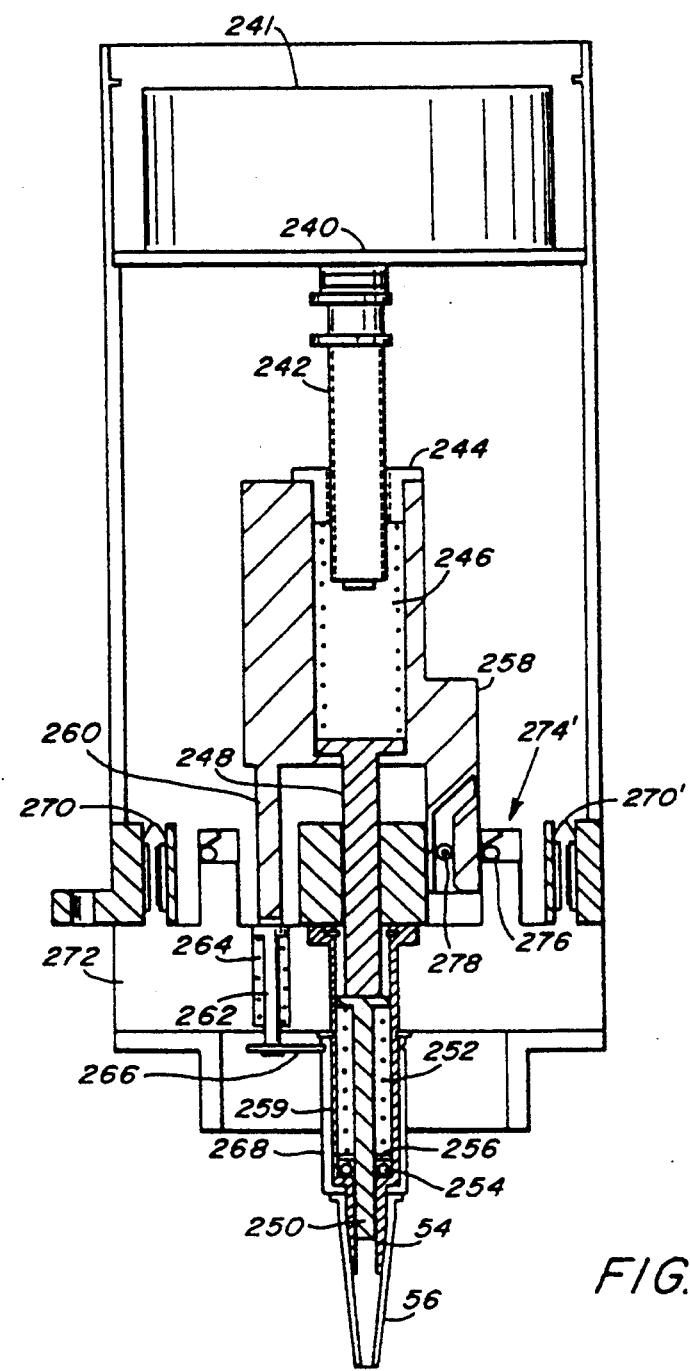
FIG. 7 is a cross-sectional view of the fluid transferring module showing the operation of the single tip fluid aspirating and dispensing mechanism.
Figure 8:
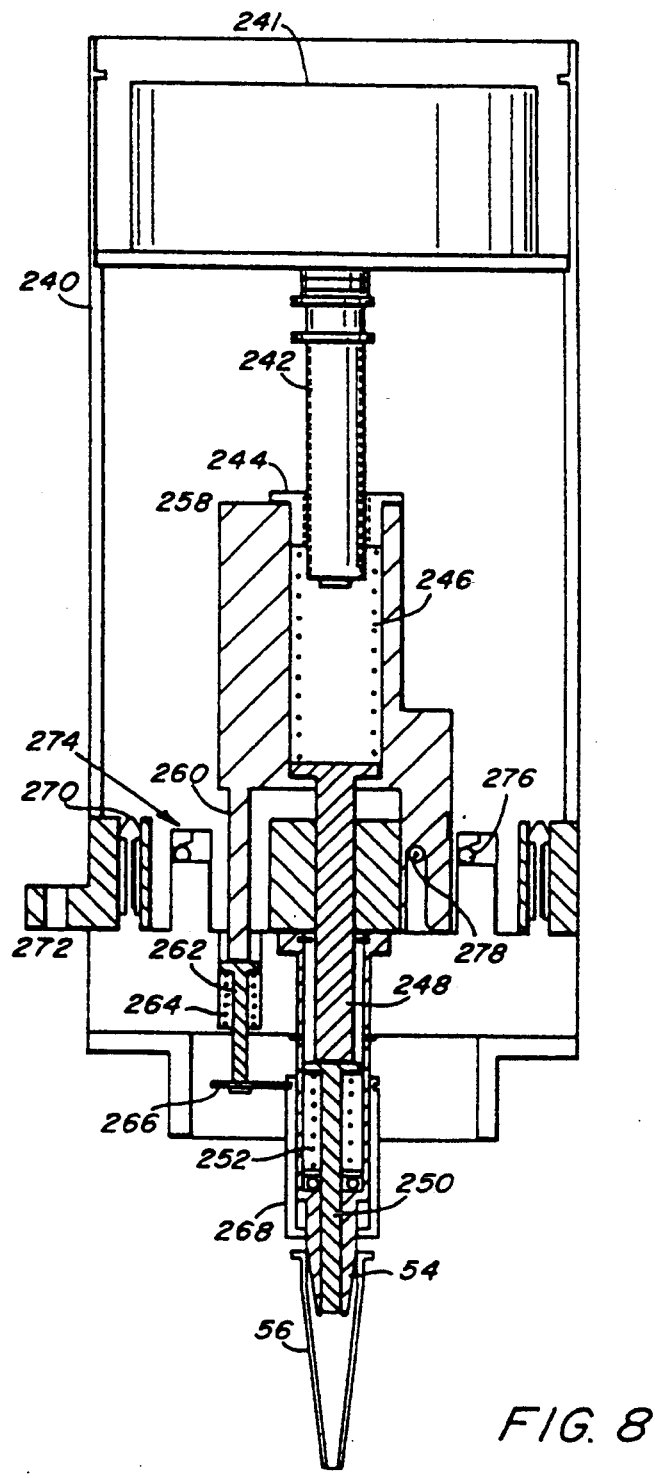
FIG. 8 is a cross-sectional view of the module change and tip, ejection system, showing the mechanism for fluid tip ejection.

An additional motor and mechanism is provided at FIGS. 6–8 to control the mechanical operations necessary to provide aspiration and dispensing of fluids. Fluid is drawn when the pipette tip 56 is attached and in place; the fluid remains within the tip 56 and never is contaminated by nozzle 54. This same motor 241 also operates as part of a mechanism which ejects the pipette tip and picks up a new pipette tip. The same motor drives the module change system by picking up and ejecting a module. Thus, pod motor 130 (FIG. 2) has a three-fold function. Firstly, it drives the displacement pump 132. (In an optical module, such as FIGS. 3A and 3B, the pod motor 130 drives a plunger which selects the optical density filter.) Secondly, it accomplishes tip ejection. Thirdly, this same motor achieves module change and replacement.

A detail presentation of the liquid dispense, tip eject, and module eject mechanism is shown at FIGS. 6–10.

A schematic representation of the automated fluid pipetting module and tip change mechanism is shown at FIG. 6. The central idea behind the operation of the module and tip eject mechanism was to devise a system of module change which utilizes only the mechanical driving devices which are already required for positioning the pod and for manipulating the samples and reagents by pipetting action. In operation and structure, a linear actuating device 231, preferably electrically driven, by a stepper motor, drives element 232 in either direction T− or T+ (reciprocatively) applying or relieving force on spring 233, which force is applied to linear element 234. Element 234, in response to applied force, can move through a distance A, until the tip end of element 234 encounters stop 235. Once stop 235 is encountered, a further application of force in the T+ direction can compress the spring 233 until the spring 233 travels the distance B.

In operation, as practiced in the invention, the range distance A is traveled to effectuate volumetric measurement and dispensing by the plunger-type pipettes. The additional travel range B is utilized for auxiliary operations such as pipette tip ejection, module exchange latching and unlatching, or other desired secondary operations.

Figure 10:
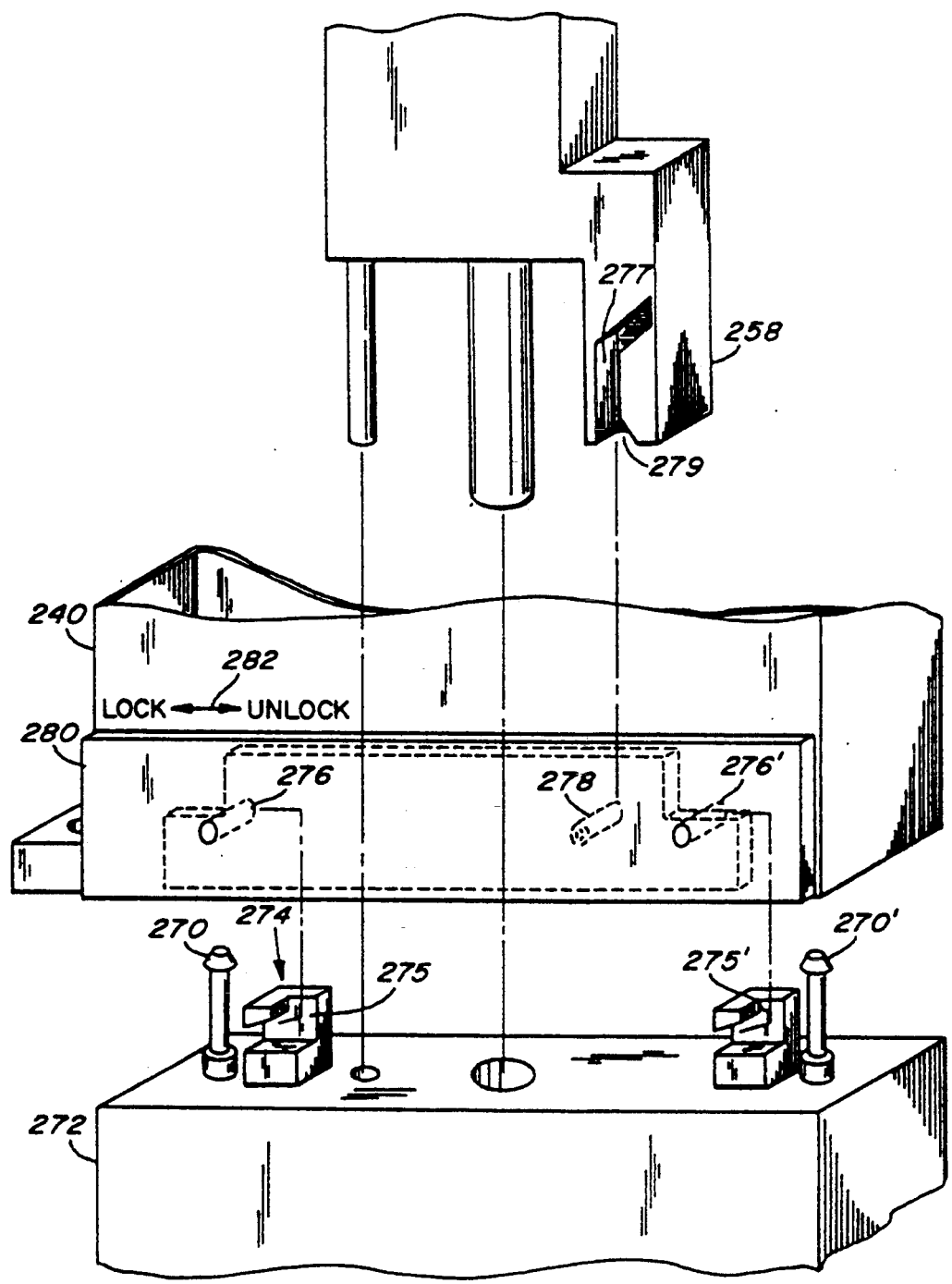
FIG. 10 shows a partial enlarged perspective view of the module changing mechanism.

When the pod 42 is positioned above a resting module, like 53, and the arm 44 securing the pod 42 descends to pick up this module, a locking mechanism locks the module into place on pod 42. The pod 42 locks an interchangeable module, such as 52, into place by action of the lead screw 242 (See, FIG. 7). After the pod 42 releases and unlocks module 52, it places module 52 in a position of rest between a pair of module holders 30. It then is moved into position above module 53 and is lowered onto the module 53. The pod 42 is aligned into position with the module 53 by alignment pins 270 and 270' (FIG. 10). As the pod 42 connects with module 53, a locking mechanism driven by lead screw 242 (FIG. 7) (to be described in detail hereinafter) secures module 53 to the pod 42. As the pod and module assembly is lifted upward, the upper leafs of the pair of module holders 30 which supported module 53 return to their original upright position, after having been spread outward when module 53 was originally positioned at rest between the holder leafs.

FIG. 7 is a cutaway view of the pod assembly coupled to a single tip liquid dispensing module. The pod frame 240 supports a digitally programmable stepper motor 241 which drives the pod plunger lead screw 242. The nut 244 is affixed to the body 258 and as the screw 242 turns within the nut 244, the plunger body 258 is raised or lowered along the vertical axis of the screw 242. Within the plunger body 258, a primary compression spring 246 is biased to normally press the drive plunger 248 towards the bottom of the central cavity of the plunger body 258.

The drive plunger 248, in turn, presses down against the top of volume plunger 250. The volume plunger 250 is normally spring loaded, pressing volume plunger 250 against the bottom of drive plunger 248. The volume plunger spring 252 (necessarily weaker than spring 246) exerts stress against the washer 256, holding in place the O-ring 254. As the plunger 250 reciprocates up and down with the volume cylinder 259, the nozzle 54, together with removable pipette tip 56, may aspirate or dispense a measured volume of liquid not greater than the volume of the pipette tip 56. In this manner, the pod and module assembly shown in FIG. 7 accomplishes the performance of single tip pipettor fluid delivery.

In the event that the operator wishes to automatically eject the pipette tip 56, the pod assembly and interchangeable module may accomplish tip removal (See FIG. 8) based upon the actions of lead screw 242. While the tip is in use, tip eject collar 268 provides a positive seat for receiving the removable tip. In this manner, the tip of pipette 56 is seated a uniform distance along the nozzle 54. By closely controlling the length of the pipette 56, the tip may be accurately positioned above or within a microtiter well.

FIG. 8 shows the operation and structure of the pipette tip ejection mechanism. As indicated earlier, the movement of the lead screw 242 down into the plunger body 258 causes the volume plunger 250 to move downward within the tubular nozzle 54. Once the plunger 250 has reached its farthest downward extension as determined by the compression of spring 252, any further movement of the plunger body 258 downwardly causes compression of spring 246 as plunger body 258 continues its downward movement; the tip eject rod 260 then engages the tip eject plunger 262, compressing tip eject spring 264 and moving horizontal linkage 266 vertically downward. This movement of linkage 266, in turn, forces the tip eject collar 268 to push down against the base of pipette tip 56, causing tip 56 to be removed from the nozzle 54. In this manner, tip ejection is accomplished. It will be noted that this tip ejection is effected with the same drive motor and screw 242, used to aspirate and dispense fluid, by reciprocating movement of the volume plunger 250.

Figure 9:
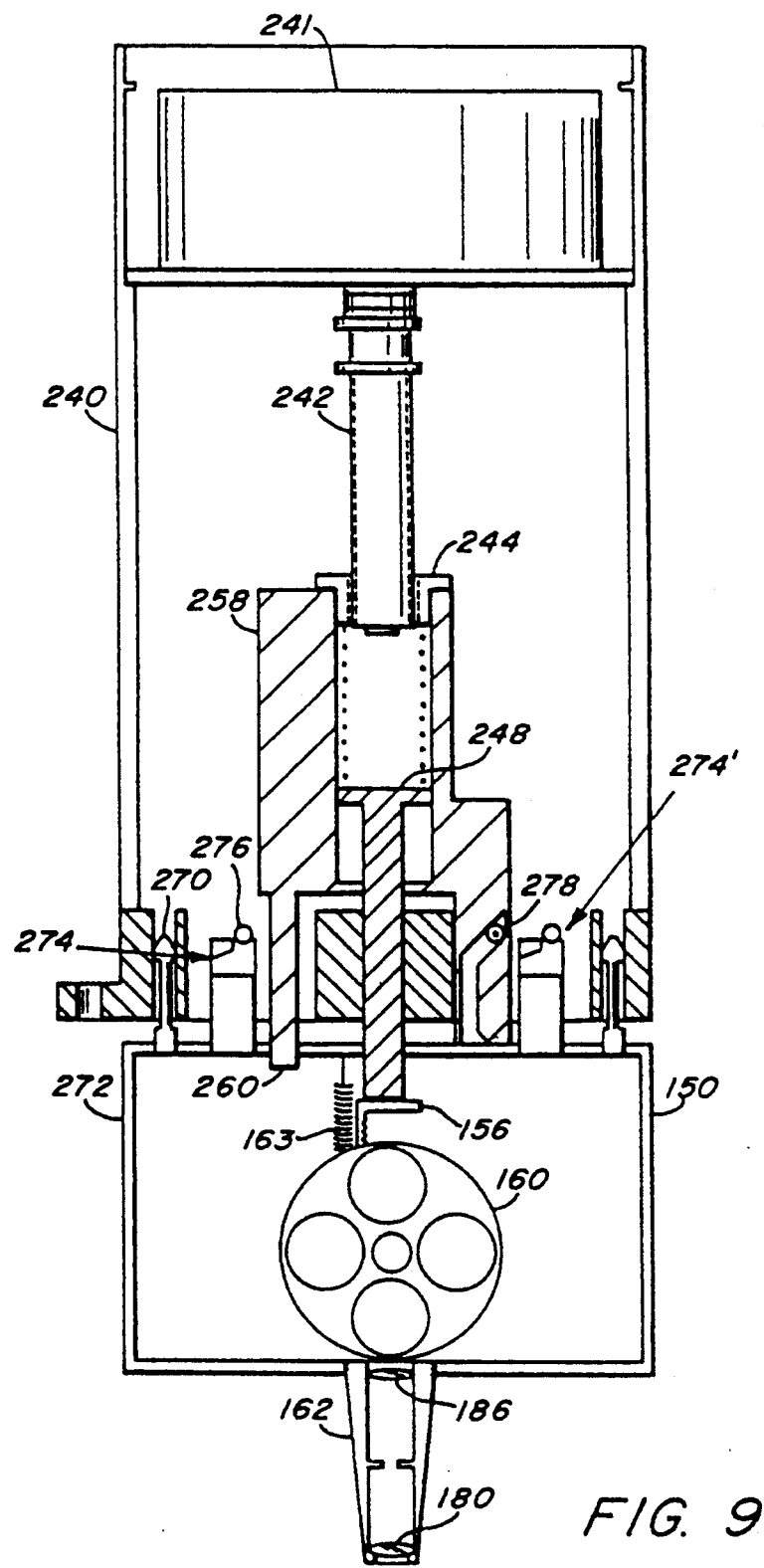
FIG. 9 shows the operation of the module change mechanism.

FIGS. 9 and 10 illustrate the structure and operation of the module changing mechanism. With reference to FIG. 10, (an enlarged view of the module locking mechanism of FIG. 9), module alignment pins 270 and 270' project up into the channels of pod frame 240 so that the module 272 is properly aligned with the pod. Module locking pins 276 and 276' (FIG. 10) are integral with a horizontally sliding module locking bar 280 and when the pins reside in channels 275 and 275' of module 272, the aligned module 272 is locked as indicated in FIG. 7. A module eject bearing 278 is mounted about a pin (not separately shown) that is an inwardly directed extension of locking bar 280. As the plunger body 258 is reciprocally driven down, the body channel 277 slides against bearing 278 (See FIGS. 7, 8, 9 and 10.) The mouth 279 (FIG. 10) of the channel 277 receives the bearing 278, so that as the channel 277 rides down the bearing 278, the module is locked to the pod; when the channel 277 rides up the bearing 278, the module is released from the pod. Locking pins 276 and 276', affixed to the locking bar 280, reside within channels 275 and 275' to lock or release the module 272 by movement of the pins 276 and 276' within the channels in a reciprocal motion as indicated by arrow 282 of FIG. 10. Sliding the bar 280 to the right unlocks the module body 272, while sliding the bar 280 to the left locks the module to the body 272. It will also be noted that the fluid dispense, tip eject, and module locking mechanism is flexible to accommodate the automatic operation and securement of a variety of modules, besides those of a fluid transport variety.

FIG. 9 also shows the operation of optical module 150. As indicated earlier, light from a sample well to be analyzed enters the module 150 through lens 180 and 186 secured within lens holding tube 162. Should a selection of different optical filters be needed, the optical filter wheel 160 can be automatically rotated by the action of the drive plunger 248. Thus, the drive plunger 248, in conjunction with lead screw 242 and nut 244, operates the optical filter wheel 160 by the same vertical movement that caused the volume plunger 250 of FIG. 7 to reciprocate. (The filter wheel 160, as explained previously, is linked by a rack and pinion drive to the rack plunger 156.) Module eject for the optical module is identical to that of the fluid module of FIG. 10. The tip eject rod 260 enters a cavity (FIG. 10) of the optical module 150 (FIG. 9) since tip eject is not needed in conjunction with the optical module.

Figure 11A:
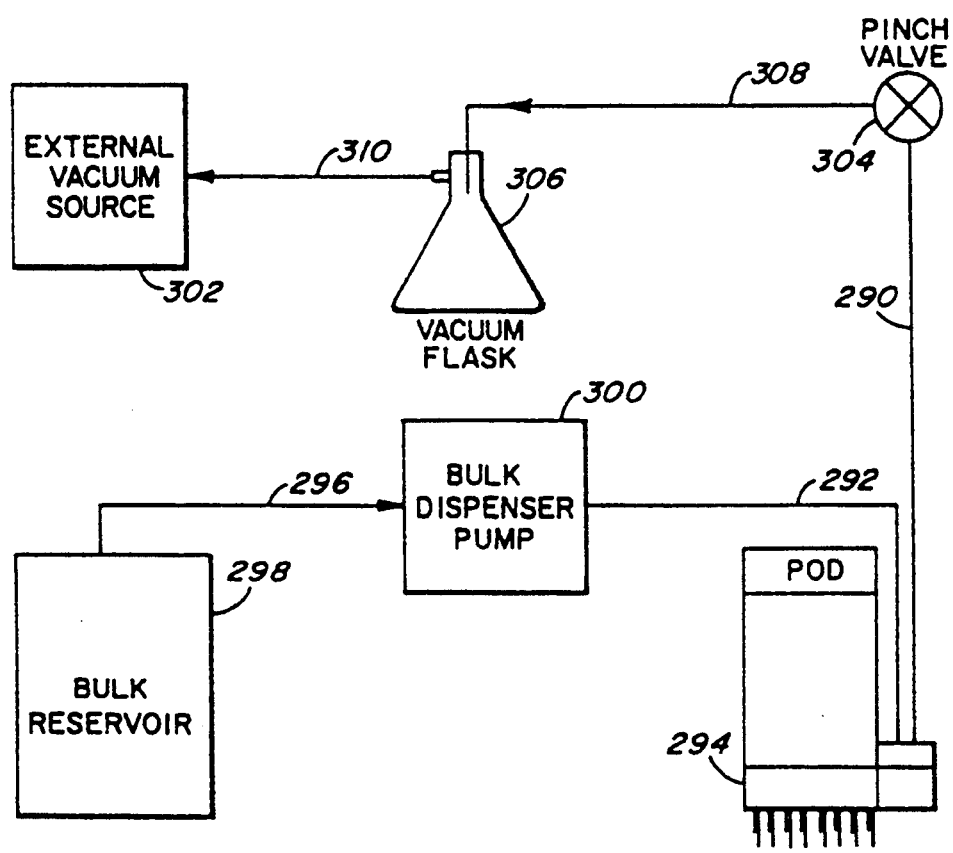
FIG. 11A shows a diagramatic view of the bulk dispense system.

With reference to FIG. 11A, the bulk dispense and aspiration mechanism is illustrated. Two sets of flexible tubing 290 and 292, are interconnected to the bulk dispense module 294 through nozzle positioned on the pod 42 (See FIG. 11B.) To dispense fluid one row at a time in bulk, fluid is drawn through tubing 296 from bulk reservoir 298, by the bulk dispense pump 300 (FIG. 11A). This pumped fluid is then transferred through tubing 292 to the bulk dispense module 294 seated at the under side of the pod. (An example of this tubing 292 and pump 300 is shown at FIG. 1.)

To aspirate and clean out one row of microtiter wells at a time, an external vacuum source 302 (conventionally found in a biological lab) draws waste fluid up through the bulk dispense module and along tubing 290 to pinch valve 304. When the pinch valve 304 is open, the fluid is drawn into the vacuum flask 306 along tubing 308 by action of the external vacuum source 302 through tubing 310 acting on flask 306. After flask 306 fills with waste fluid, it may be disposed conventionally. By automatically controlling the action of the pod and module 294, one can program the work station to wash and clean a complete microtiter plate in a short time. This bulk dispense and aspiration system may be used to "prime" the bulk dispense module 294 as is typically required in assay applications.

Figure 11B:
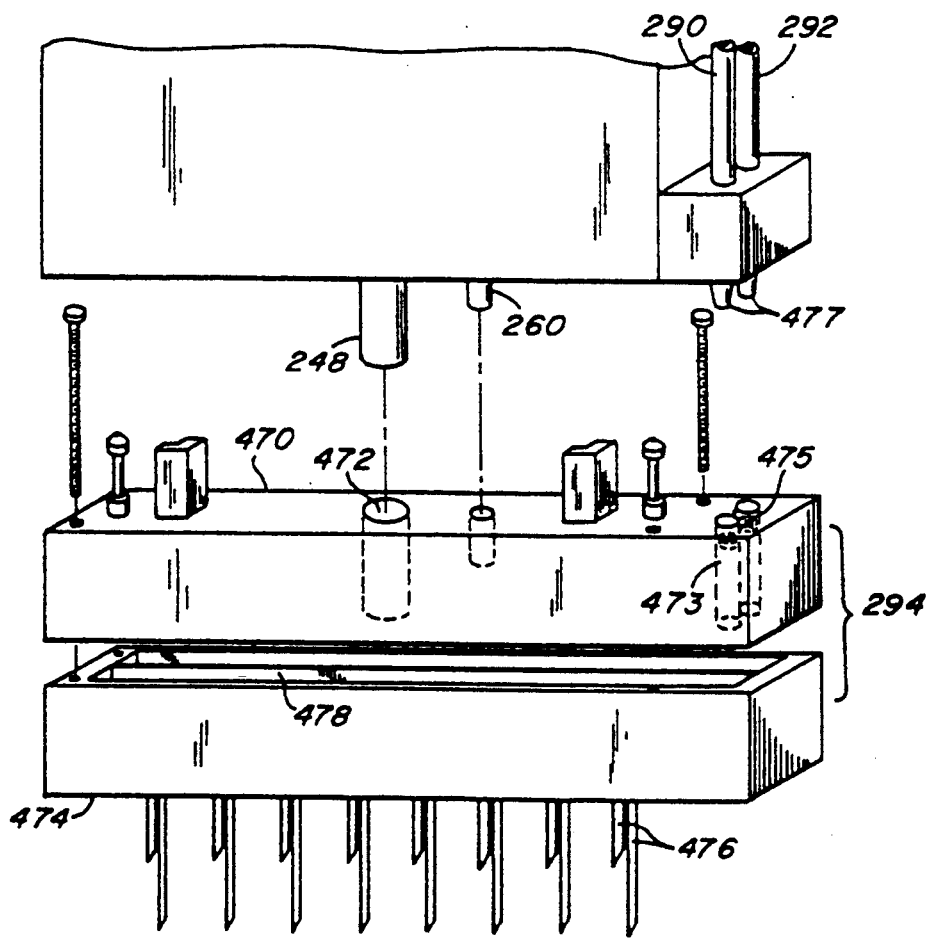
FIG. 11B shows an exploded perspective view of the bulk dispense module with multiple well filling capacity.

With reference to FIG. 11B, a perspective view of the multi-well bulk dispense module 294 shows an upper compartment 470 with a hollow cylindrical receptacle 472 for receiving the pod drive plunger 248. As the drive plunger 248 extends into the body of the upper compartment 470 of the bulk dispense module, the pod compression spring (FIG. 8, 246) biases the plunger 248 against the bottom of receptacle 472. The bulk dispense module is locked into place in the same manner as shown at the module changing mechanism of FIGS. 9 and 10; but, the bulk dispense module releases as the pod compression spring 246 extends upon release of bearing 278 from channel 277, there being no internal springs in the bulk module itself, unlike the single or multi-tip pipette carrying nozzle modules.

The lower compartment 474 of the bulk dispense module 294 has at least a pair of needles 476 extending downward, one longer needle to aspirate and a shorter needle to dispense liquid for each well. This module may have a single pair of needles 476 to service one well or be configured for multi-well servicing (eight wells) as shown in FIG. 11B.

Figure 11C:
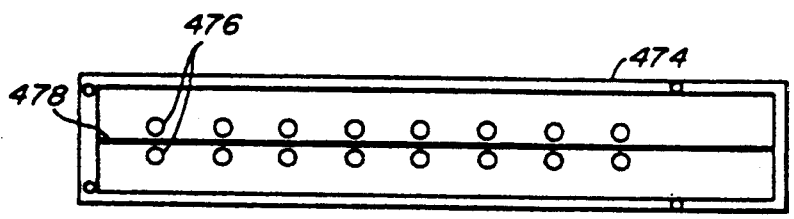
FIG. 11C shows a plan view of the lower compartment 474 of the bulk dispense module of FIG. 11B.

FIG. 11C shows a plan view of the inner lower compartment 474 of the bulk dispense module 294. A partition 478 separates the aspirating needles from the dispense needles, for purposes of maintaining sanitation. By having a removable compartment 474, the bulk dispense module 294 is easily serviced and cleaned. Fluid is transported through the upper compartment 470 at conduit 473, so that fluid will fill one of the lower compartment chambers separated by partition 474 for dispensing through needles 476. Fluid is aspirated up from the other lower compartment section partitioned by 474 through the remaining conduit 475. Conduits 473 and 475 may have O-rings or other suitable seals seated at their top ends for sealing and receiving the nozzles 477 connecting flexible tubing 290 and 292 to the bulk dispense module 294.

The computerized operating system for the automated multi-purpose analytical chemistry processing center and laboratory work station, in the preferred embodiment, is split between the EIU 35 and the computer 39. The operating system controls the overall operations of the work station and is organized to perform a biological experiment or chemical assay through an orderly presentation of programmable instructions which direct the movement, Measurement Functions (as described hereinafter), and operation of the work station as shown in FIG. 1. The instructions for an orderly performance of the biological or chemical assay are provided, in part, by preprogrammed instructions resident in the operating system, and, in part, by additional instructions or parameters supplied by the user in response to questions presented by the operating system.

The operating system for the automated laboratory work station of this invention may be divided into three sectors: (1) "building" the experimental assay instructions, (2) "running" or executing these instructions, and (3) a set of utilities.

In order to perform a useful experiment or assay, it is necessary for the operating system, with the cooperation of the user, to create or build a set of instructions which regulate every step of the work station's performance for the entire experimentation. Once this set of instructions is completed, and arranged in a string of sequential bytes of information for interpretation by the operating system of computer 39 and the EIU (electronic interfacing) 35 in a conventional manner, these instructions are processed by the run or execute sector of the operating system so that the automated and remote controllable components of the work station may implement the instructions.

Utilities representing an adjunct segment of the operating system which may be useful in calibrating a transducer, such as the optical density module of FIG. 3A; or, for editing the set of instructions prepared during the build sector before these instructions are executed. Utilities also include setting a clock to provide a real time frame of reference for the entire period while the experimentation is proceeding.

The interrelationship of the operating system's major sectors of building, executing, and utilities as above described may be best illustrated by the analysis, in detail, of an example of an experimental step of an assay that might be performed using the laboratory work station and the operating system of this invention. A biological investigator might be interested in determining how two different strains of bacteria each react to a single chemical reagent. (The steps illustrated show the manner in which the command instructions are built, and does not necessarily reflect an application of the work station associated with any particular assay test.) In order to perform such an experiment using the automated laboratory work station, the experimenter or user would arrange a configuration of the table 28 (FIG. 1). The user might place the tip rack 26, the modules 53, and the microtiter plate 27 in the positions shown within compartments of the table 28. The remaining open compartments as shown in FIG. 1 of the table 28 might be used to house removable fluid reservoir containers. In each of these containers a different strain of bacteria might be placed. A chemical reagent that is to be provided may be made available through use of the bulk reagent pump 134 (FIG. 2).

In building a set of instructions that will enable the computer 39 and the EIU 35 to run the experiment, the user must inform the operating system how table 28 has been configured. A pictorial representation of table 28, showing its compartments and the module holder 30 locations, is presented on the screen, and the user is queried to indicate (by keystrokes at the terminal or a "mouse") the desired configuration of modules, the microtiter plate, and tip rack. The user then configures the symbols on the screen to arrange the table 28 in the same manner as he has initially placed the research implements on the table 28. A series of menus are then presented on the computer screen showing a listing of retrievable files to the user which are part of the experimentation instruction building phase. In this case, the entire experimentation may be stored as a single method. As used in this application, the term "Method" is a string of sequentially arranged preprogrammed instructions which in their totality represent all, or substantially all, the instructions necessary to perform an entire assay or a significant portion of an assay. Methods may be divided into "Procedures". "Procedures" are defined by the user to be a subset of instructions which when strung together form a Method. The operating system in the preferred embodiment is programmed to request that a new Procedure be established each time there is a need to change the configuration of the table 28. In the example being described, the Method and Procedure may be one and the same, but they need not be. This categorization is up to the user to decide.

In order to configure the microtiter plate 27, the tip rack 26, and the two fluid reservoirs on the table, the user supplies information to the operating system in answer to questions presented on the computer screen. The entire set of instructions needed to fully inform the operating system of the location of implements on the table 28 is called a "Configuration Function". For example, the operating system queries the user as to the configuration or arrangement of the tip rack 26, microtiter plate 27, fluid reservoirs, and module locations (where the modules 53 are stored) in relation to each other and their placement within the compartments of the table 28 (FIG. 1). The user responds to the system inquiry by keystroke or an electronic pointer or mouse, telling the system where the rack, plate, reservoirs, and modules are positioned. When used in this application, a "Function" may be defined as an elementary set of programmable instructions which carries out a complete task such as "configuration", that task being a necessary step in building an entire procedure or method. Additional examples of "Functions" include "Pause" (where the work station stops for a set period of time); "Agitate" (where the tray 28 reciprocates along axis 40 to shake the wells in microtiter tray 27); "Tip Change" (in which disposable tips are changed); and, "Message" (where a message may appear on the computer screen or print-out by the user as a means of describing the experiment as it progresses during the "RUN" sector). "Procedures" are built from a string of sequentially arranged "Functions"; and "Methods" are built by a string of sequentially arranged "Procedures".

Once the Configuration Function has been entered into the computer 39, informing the operating system of the manner of table configuration during the experimental Method and Procedure, the user has built the first Function of the programmable instructions necessary to carry out his biological assay. The next step in instruction building is to provide the information necessary to build a Bulk Dispense Transfer Function. In the example, under discussion, the user has chosen a chemical reagent flask connected to the bulk dispense system so that the chemical reagent may be distributed to a plurality of wells on the microtiter plate 27 through use of the bulk dispensed module as shown in FIGS. 11A through 11C. In order to build this Bulk Dispense Transfer Function, a series of questions will be presented by the operating system to the user and the computer 39 screen. The user will be asked to select a module for performing this Bulk Dispense Transfer Function for transferring fluid. He will indicate his choice as the bulk dispensed tool. The screen will then present a drawing or map of the microtiter plate and its 96 well configuration. A standard microtiter plate may have, for example 96 wells arranged in an 8 by 12 matrix. The operating system has defined each row of 12 wells along a line parallel to axis 40 of FIG. 1 to be an "row" and a line of 8 wells parallel to axis 50 to be a "column". In this example, the user has chosen to bulk dispense the chemical reagent into two columns of 8 wells each. The 8 well dispense module, when attached to the pod 42, may, in conjunction with the bulk dispense system as illustrated in FIG. 11A, dispense chemical reagent from a flask off the work station table (not shown) into all 16 wells, one column of eight wells at a time. The information needed by the computer 39 to perform the operation of this Function will have to be supplied by the user to the operating system in order to build the Functions. For example, when undertaking the Bulk Dispense Function of filling all 16 wells with Chemical reagent, the operating system may ask the user what volume of reagent is to be dispensed into each of the 16 wells. Once all the questions necessary to perform the Bulk Dispensing Function have been asked the user (Transfer Functions, of which Bulk Dispense is a type, will be discussed in detail hereinafter), the Function has been built, and the system then goes to a new set of menus on the screen so that the user may complete the next Function in this experiment. (The user may wish to "prime" the Bulk Dispense Module by building a "priming" Function. This function causes the Bulk Dispense Pump to displace and purge all air or waste fluids from the Bulk Dispense System.)

The third Function to be built as part of this single procedure method for performing a chemical experiment is a new Transfer Function. The user will provide information to the operating system in order that the work station may automatically add biological specimen to the reagents now resident in the first two columns of microtiter plate 27. The user will instruct the operating system that he wishes to change modules and select an 8 tip pipettor. The operating system will automatically place a fresh set of disposable tips 56 on each of the 8 nozzles of the multi-tip pipettor. The user will then instruct the operating system that the multi-tip module will proceed to a first reservoir for aspiration of sample specimen of the first bacterial organism into each of the disposable tips. (Each type of the bacterial organisms are present separately in each of the two reservoirs (not shown) configured on table 28). The user then instructs the operating system to transport the aspirated bacterial specimen to a first column of wells on the microtiter plate 27, where the multi-tip pipettor will dispense specimen simultaneously into the eight wells of the first column. This completes this Transfer Function. The user then continues to build a set of instructions by creating a "Tip Change" Function; wherein, the user instructs the operating system to change the tips by disposing of the tips which have aspirated the first bacterial specimen and replacing them with a set of 8 fresh tips from the tip rack 26. (Alternatively, the tip change may be automatically performed as part of the Transfer Function.) At the completion of the tip change, this function is added to a string of data necessary to build this single procedure method. "Tip Change" may be accomplished by answer to a "tip change" question that is part of the Transfer Function.

Once the fresh tips are in place on the 8 tip pipettor, a new Function will be built instructing the operating system to cause the work station to aspirate liquid from the second reservoir ("a Source Location") containing the second bacterial sample and dispense this liquid into each of the 8 wells ("a Destination Location") located in the second column of the microtiter plate. Once this set of instructions is completed, another Transfer Function is built and the specimens may be fully distributed into wells containing the test chemical reagent solution, once the instruction set is run. A new Function is built by user reference to a series of menus, and a selection of the Function type from the menus.

The next set of instructions necessary to place into the operating system is a Function that will cause the machine to idle or "sleep" for a period of time sufficient for the bacterial cultures to incubate in each of the microtiter wells. In order to build this function the operating system presents questions to the user as to the length of time the user wishes to allow the system to rest, allowing the bacterial cultures time to incubate. During this "sleep" time those two columns containing the experimental solutions will remain undisturbed by the laboratory work station. The work station may remain at rest or be completely free to carry on an entirely different experiment or to run another Procedure within a larger experimental Method.

Once the parameters for the "sleep" and incubation time function have been entered into the operating system, it is necessary to build a Measurement Function for measuring a physical characteristic of each of the 16 wells. In the preferred embodiment, the measurement module is the optical instrument as shown in FIG. 3A through 3D. As part of the set of instructions necessary to run the entire experimental assay, a new Measurement Function must be built by choosing the Function from a menu, wherein the work station will be ordered to remove the fluid dispensing pipettor and replace it with an optical measurement module. The user would again see a map or illustration of the 96 well microtiter plate 27 on the computer 39 screen and in a conventional manner, by keystroke, identify (according to a rectilinear co-ordinate plot) for the operating system which of the 96 wells are to have optical measurements performed. In the operating system definitions, this manner of identification of the location of the wells of the microtiter plate 27 that will be visited by the optical measurement module is defining a "range". Additionally, the operating system would query the user to identify for each well a preferred or optimum measurement reading the system is to identify. For example, the user must inform the operating system to identify and store information concerning the location of any of the 16 wells being measured that indicate an optimum optical density reading. If optical density were measured on a scale from zero to two, the user might inform the operating system to identify all wells that show an optical density reading from 1.3 to 1.5, This instruction to retain in memory information concerning optical density readings for each of the 16 wells would complete the instruction set necessary to build the Measurement Function. Those wells which measure a 1.3 to 1.5 reading, in the present example, become defined as an "array" of wells within the selected "range" of wells visited.

After the optical density Measurement Function instructions are loaded into the operating system during the "build" sector, the user would be required by the operating system to instruct the system to change modules again and use a single tip pipettor having a fresh tip. The user could identify for the operating system which of the 16 wells are to be aspirated and transferred to a new location in the microtiter plate. This identification is the result of the optical density information stored in memory by the operating system in accordance with the Measurement Function. Thus, a new Transfer Function could be built where the "source" (beginning location) of the wells that are to be transferred are identified according to optical density measurement information, i.e., the "array" is defined during the "run" sector. This source location information, of course, is not known to the experimenter during the build sector but the movements that need to be taken by the work station to achieve identification of those desired wells having an optimum optical density reading may be preprogrammed during the build phase and called an "array", the member wells being found and identified during the "run" sector, making the system one with feedback resulting from real time measurements. The experimental assay may be preprogrammed to proceed according to measurement parameters, not known at the time, so that the Method is being built with not every parameter known when "run" begins, but the parameters are later found from optical information available once the assay program is "run".

Thus, the final Functions that will complete the building of this exemplary single Procedure Method require the building of a Transfer Function that will transfer specimen from the plurality of microtiter wells which show optimum optical density readings as defined by the user to a new well location for further study. These new locations may be selected by the user reserving wells as the destination for transferring specimen from existing wells showing optimum optical readings. In this example, the user may build a Transfer Function which first moves specimen from the first column, which contained a first type of bacteria, to new wells where the colony of bacteria will be free to further grow and multiply. After transfer of those wells with a desired optical reading from the first column is made, a new function may be created which designates a tip change, or the tip change may automatically be built into the Transfer Function, so that a fresh tip 56 may be used, allowing the single tip pipettor to aspirate specimen from the second column containing the second strain of bacteria to other new well locations on the microtiter well. For purposes of illustration, let us assume that the user, by accessing the operating system, builds this Transfer Function so that those specimens showing a greater optical density contained within the first column be transferred on a one to one basis to the third column. Thus, if the optimum density reading occurred in three out of the eight wells of the first column, three new wells of the third column would be the destination for the transfer of fluid from those optimum wells in the first column. Target optimum wells have a designated column designation location, in our example, but the number of wells transferred to that destination is unknown during the build sector. This number will be discovered through optical measurement during the run sector. Likewise, those wells in the second column which show desired optical parameters may be aspirated and transferred to new wells in the fourth column.

In the operating system as designed by the Applicants, a Measurement Function is built where the "range" (those wells visited by the measurement module) is defined as the sixteen wells of the first two columns of microtiter plate 27, while the measurement "array" (wells which are members of the "range" set, selected from the "range" having a certain optical characteristic) is made from an unknown well membership during the building sector. The wells belonging to this "array" will be defined during "run" time, based upon optical criteria stored in another portion of the Measurement Function. When the user builds the Transfer Function which transports the optimum wells to new locations, the user will simply refer to this same "array", by an identifying number or name, as the group of wells which constitute the "source" of fluid transfer.

The preceding example of using the operating system to assist the user in building an entire Procedure is made for purposes of illustrating how the user interacts with the operating system to build a string of Functions which when sequentially tied together in an orderly manner comprise a Procedure which in turn may comprise a Method. (This example may have been the first step in a MIC (Minimum Inhibitory Concentration) Assay, an experimental procedure well known in the clinical arts.). Alternatively, the antigenic susceptibility of specific enzyme secreted in the bacterial medium, resulting in color changes in the microtiter plate wells, may be the subject of the application of the work station. If the user wishes to proceed further with the experimentation and reconfigure the table, he will be asked before creating a new Procedure within the Method if the operating system needs to be told that there is a reconfiguration of the table. He then continues building the one Procedure Method, Function by Function. For example, after the user has identified desirable sample for further growth he may wish to further bulk dispense more reagent into new columns 3 and 4 to see what level of concentration would kill or otherwise endanger the bacteria colony. Optical readings might be indicative of bacterial colony growth. For example, an optical density reading which is indicative of the absorbance or blockage of a great quantity of light would indicate that the colony has grown and thrived. An optical reading that shows a low absorbance would be indicative of a bacteriologic colony that was unable to survive in the chemical reagent. If the user wished to remove one of the bulk reservoirs from its compartment holding and replace it with a reservoir containing a second reagent, he would be reconfiguring the table and thereby may begin building a new Procedure within the experimental method; or, he may continue within the same Procedure.

In the building sector, it is the Function set of instructions that are the building blocks for forming a complete experimental Method. Most Functions, such as "tip change" or simple fluid transfers are formed according to a preprogrammed set of instructions resident in the operating system. But if the user wishes to transfer fluid in a manner that is not prestored in the operating system, a programming technique would be needed for creating new Functions, yet without interfering with the overall general structure of the build sector of the operating system.

In the preferred embodiment, those Functions, such as the Transfer Function and the Measure Function, which may be executed in a variety of manners are built by using "templates". As used in this application, the term "template" may be defined as a byte string of information used by the operating system to selectively question the user for purposes of creating a Transfer or Measure Function. Although the Transfer Function may be carried out in a variety of manners, such as transferring fluid from one column of wells to an adjacent column of wells on a one-to-one correspondence, it is clear that there exist a wide variety of fluid transfers.

"Aspiration" is one form of fluid transfer, where fluid is removed from a reservoir or well. "Copy" is a transfer function where duplicate of an existing set of wells is created at a new location by transfer of part of the fluid resident in the "original" wells. Another type of transfer function is "reservoir to wells", where fluid is transferred from a reservoir to a sequence of wells. Other transfer functions include "wash plate", "serial dilution" and "well-to-well" transfers.

Rather than supply the operating system with every conceivable Transfer Function that might be used to perform a chemical or biological assay, the inventors have developed a system whereby the user, interacting with the operating system, may create Templates which are then usable to build functions of a unique but specialized variety, not previously present in the system software.

Figure 14:
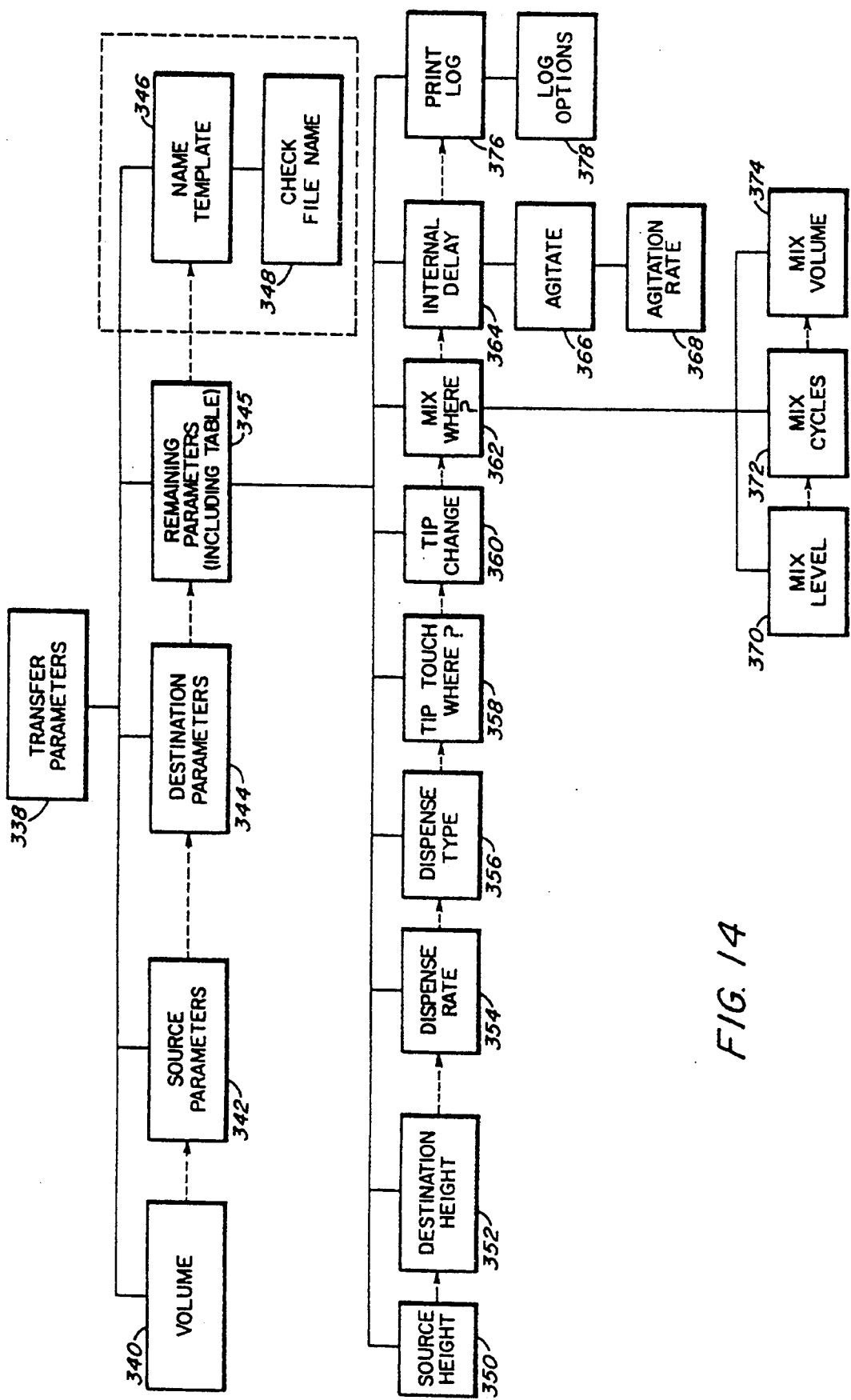
FIG. 14 is a block diagram illustrative of the production of a Transfer Function.

The operating system is structured to be able to build and define a Transfer Function based upon the answer to a selected number of questions. FIG. 14 illustrates, in conjunction with FIG. 12, how questions may be presented to a user by the operating system necessary to build a Transfer Function. In order to build a Transfer Function which when run or executed by the operating system will perform a fluid transfer, transfer parameters 338 must be supplied to the operating system. The questions that need to be answered include questions concerning volume 340, source parameters 342, destination parameters 344, and any remaining parameters 345 (as described hereinafter) including those parameters which may be fixed for this Procedure and for this Method. The operating system queries the user as to the height of the source 350, the destination height 352, the dispense rate 354 and the manner of dispense (whether every drop of fluid should be "blown out") or dispense type 356. The user is asked whether pipette tips are to touch the side of the microtiter plate wells 358 ("tip touch") and where cross-contamination is a concern, whether tip change 360 is needed. "Mix" is defined by the operating system to be a fluid transfer where fluid is aspirated out of a well and dispensed immediately back into the same well, and includes questions 362, 370, 372, and 374. The user is asked by the operating system which wells are to be mixed 362, the level of mix 370, the cycle of mix 372 and the volume of mix 374. The user is requested information on whether to agitate the contents of a well 366 and at what rate of agitation 368, for example, by moving the table 28 back and forth along axis 40. The user is asked whether he wishes to make a transfer at a certain rate; i.e., transfer fluid from a set of source microtiter wells to a set of corresponding destination microtiter wells at a particular rate, i.e., wells per minute. If the user wishes to keep a record of the experiment and the nature of the movements and measurements taken, he may print a log 376 and have the option 378 to display the information only or display and print.

Figure 12:
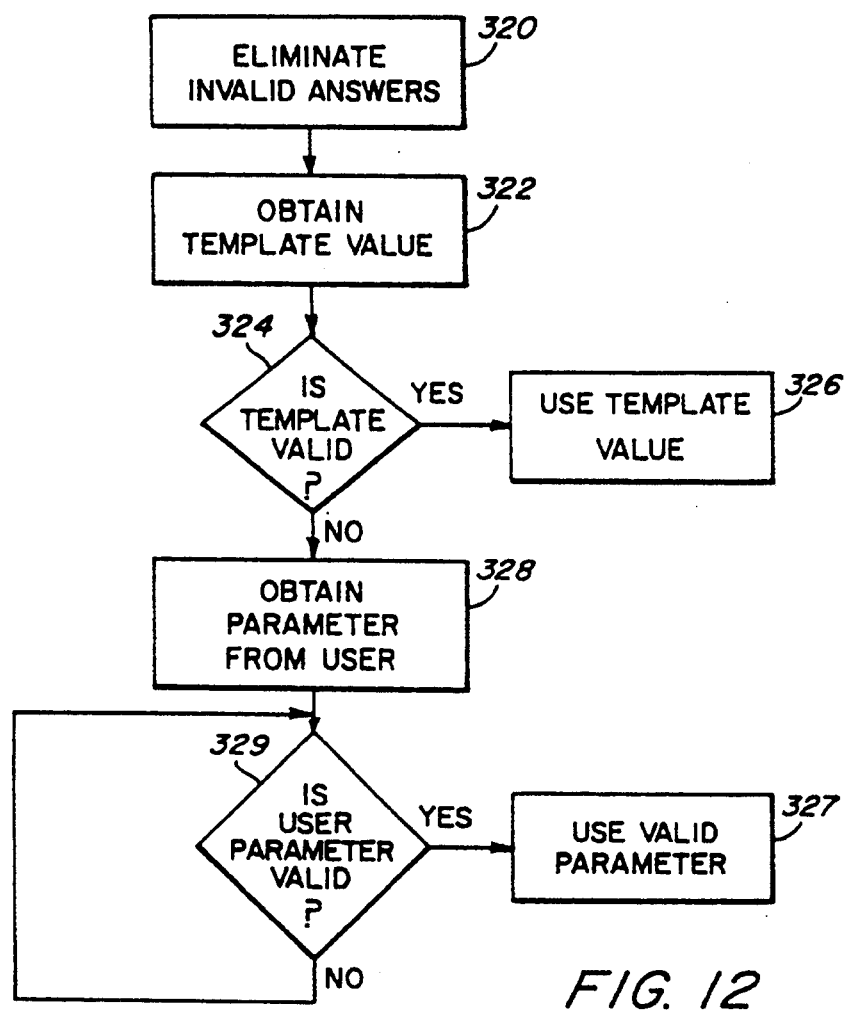
FIG. 12 is a flow chart of the template selection protocol for the workstation computer operating system.

As each question necessary to build a Transfer Function (FIG. 14) is presented to the user, the operating system steps through in orderly protocol in order to finally supply the information to build the Transfer Function. FIG. 12 shows the decisional steps taken by the operating system at each question listed in FIG. 14. For example, assume the user wishes to transfer a specific volume 340 of liquid. If the total volume which the microtiter tip 56 (FIG. 1) is capable of transferring is no more than 50 microliters, then the operating system would eliminate invalid answers (320) beyond the limits of the fixed parameters of the laboratory work station (FIG. 12), such as answers supplied by the user which accidentally exceed the volume capability of the microtiter tip. Before determining whether the volume question 340 need be presented to the user at all, the operating system would search the template that is being used to create the Function to determine whether or not prestored within the template, a template value 322 for the fluid volume 340 already existed. The operating system would then determine whether the template value 324 was usable or invalid. If the template value is valid, then the template value is used (326). If, the template value is not valid or the template being used to create this particular transfer function directs that the user be questioned, then the volume parameter is obtained from the user 328. If the volume parameter is valid 329, then the operating system uses that parameter 327 to build the Function. If the value supplied for volume by the user is not valid, then the user is questioned again to supply a valid value 329. In this manner, it is clear to see how a template may be used to build a transfer function in a short amount of time with a minimal amount of user interface.

Let us assume that the user wishes to perform a transfer by building a Transfer Function that heretofore has not existed in the operating system. The laboratory work station of the preferred embodiment has template software resident in a file stored by the operating system which may be used to build specialized Transfer Functions, such as "well-to-well" transfer, "serial dilution", and other Transfer Functions previously discussed. In order to create a custom made Transfer Function of a type which is not already stored within the operating system file, the user may call upon the operating systems' Generic Template to create a new template. The new specialized template, when created, will present a smaller number of questions to the user when the user wishes to create a Transfer Function than would be presented if the Generic Template were used to build a Function. The new Function would be useful in the performance of a fluid transfer of a manner not heretofore stored within the operating system. In order to create a new Template, the operating system would present questions to the user in the same manner as previously described and shown at FIG. 14; however, in addition to the questions presented the user heretofore discussed, once the template was filled with data and created, it would be given a name 346 and the operating system file memory would be checked 348 to make certain that the template name is available for storage. Once the template is created, it may be used later in the same Procedure or a different Procedure, or another Method, to create and build a Function according to this new specialized template. Only the Generic Template may be used to build new specialized templates. Another factor in building a template which differs from building the Fluid Transfer Function is that the answers to questions necessary to build a template do not have to be fixed parameters, but may be "ask the user". For example, while building a Template for creating a unique Transfer Function at a particular flow dispense rate 354, the user may supply the operating system with a fixed answer setting the dispense rate. Having this fixed answer, when the template is later used to build Functions, all of which, if built from this template, will have the same dispense rate. Questions concerning dispense rate will never be asked the user when this new template is, in turn, used to build a Transfer Function. Where the user wishes to allow different volumes of liquid to be transferred in Functions built according to this custom-made template, when creating the template, the answer to the volume question 340 will be "ask the user". The template becomes a custom-made sub-set of operating code used to build Functions, but the template inherently limits the questions presented to the user to be only those questions asked, as in FIG. 14, which are flagged in the template as "ask user". Template creation is a utility, and need not occur during the "build" sector of the operating system. Thus, when a Function is built which uses this newly created template, the user will always be asked the volume 340 (FIG. 14) he wishes to transfer.

Figure 13:
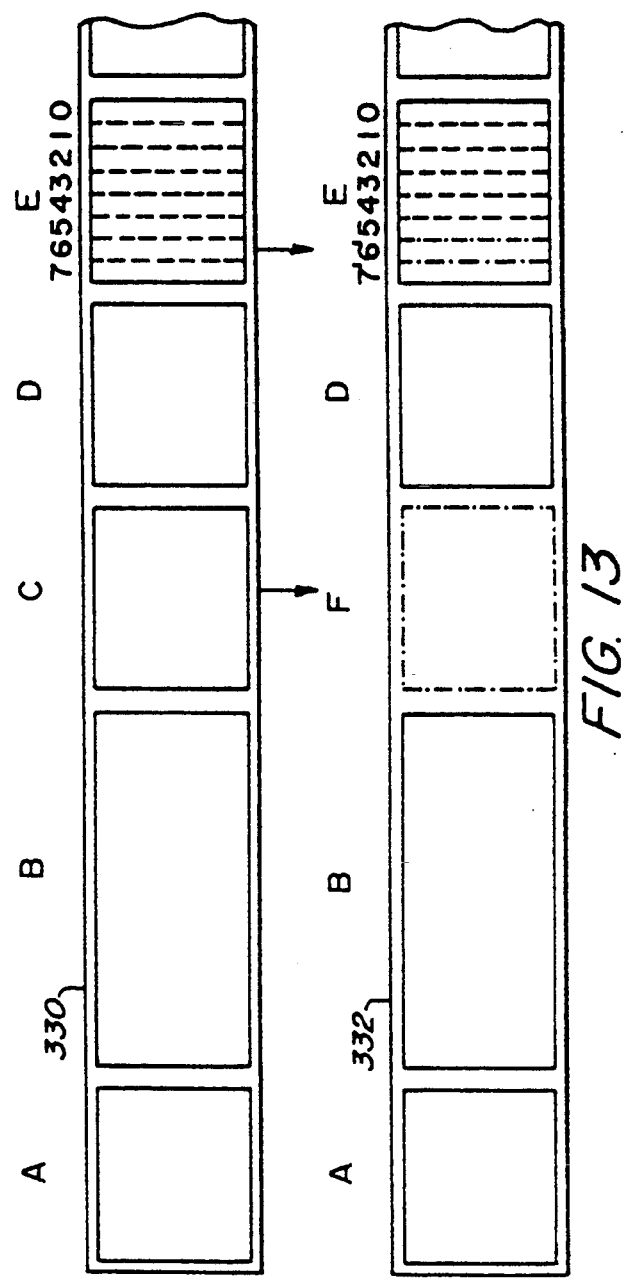
FIG. 13 is a diagrammatic illustration of the function building process of the workstation computer operating system which occurs at each step of FIG. 14.

The unique methodology illustrating the operating system's ability to make use of Function building by templates is illustrated in FIG. 13. Template 330 is shown as a string of information sequentially arranged for loading into the operating system and is a specialized template built from the Generic Template. In this figure, the template 330 comprises information bytes A, B, C, D and E. A "byte" has eight bits of data. In byte A, for example, a fixed parameter is stored which determines the dispense rate during fluid transfer. Byte B might determine how high within the well (350) (FIG. 14) the work station must position the pipette tip. The information contained in the template 330 at bytes A and B is fixed; byte C, however, may be reserved for volume data and within the template 330, byte C flags the message "ask the user". In a similar manner, byte D of template 330 is fixed information concerning, for example, the mix level parameter 370. This data will not change within any Function that is built according to template 330. Byte E contains information which is stored at the bit level. The information contained in bits 0–5 may be fixed, while the information stored at bits 6 and 7 of byte E may indicate "ask the user".

Function 332 is a Transfer Function built according to the questions presented by template 330. In order to build function 332, the user first retrieves from the operating system the template 330 by its template name (See 346 and 348 of FIG. 14). Once called out of storage, this template 330 may be used to build function 332. In the example shown in FIG. 13, the information contained in bytes A, B and D are pre-set and so function 332, at its bytes A, B, and D, has parameter data identical to that stored in the template 330. For example, a Measure Template contains information as to its name by type, like "optical density or pH meter". Data in byte A, which names the Template, simply transfers that name into the Measure Function built from the Template. Likewise, the length of the field comprising the Function is fixed by the Template, and the user need not supply this information to build an optical Density Measure Function. Likewise, a Fluid Transfer Function has a name and byte field length, but this information is fixed in the Transfer Template, and when the Transfer Function is built, the system need not query the user for these parameters. Byte C of the template, however, stores data which causes the operating system to prompt "ask the user" when data to fill byte C of the Function 332 is being built and stored. Thus, when the template 330 format of inquiry is presented by the operating system to the user, the system will immediately ask the user the questions not answered in template byte C, e.g., the volume of fluid the user wishes to transfer. The particular volume of fluid which the user wishes to transfer is built into Function 332 at byte location F in the form of a fixed parameter which is valid only for this function 332, but not for all functions built according to template 330. If by accident, the user presented a value for storage at location byte F in the function 332 which was invalid, i.e., an excessive volume amount, the operating system, in accordance with FIG. 12 (327) would again "ask the user" to supply a different parameter for volume; one that is legal as defined in the operating system. Thus, when the user is using template 330 to build a new function 332, he never is questioned by the operating system about information necessary to build bytes A and B. That information is already fixed by the template 330. The first question that the user sees is the parameter question presented at byte C. In answering the question, the user builds the information stored at corresponding byte F.

Likewise, byte E represents a set of questions which have different answers stored within the same byte. The user is never questioned as to the answers that need to be placed at bits 0–5, since they have been prestored by the template 330. The "yes, no" answer to a question located along the template at its bit 6 is supplied to bit 6' of byte E of the Transfer Function 332. Bit 7 is reserved in the template to create the answer "ask user" (coded "11" in binary), and flags the need to "ask the user" each time a new Function 332 is built according to the template 330. At a minimum, the template must use two bits storage capacity, and the Function must reserve the two-bit-wide positions, to answer a single "yes, no" question. This is because, in the template creating process, such as 330, even a "yes, no" question may have one of three binary coded answers: "yes" (01), "no" (00), or "ask user" (11). Thus, if a "yes, no" answer were stored at bit 6' of byte E of the function string 332 built according to template 330, the bit place 7' would have to be held in the Function so that the Function would match the structure of the template 330 from which it is built. Since, in building the template 330, the user chose to leave as a variable the answer to the question located at bits 6 and 7 of the template 330, a place holding binary digit "1 or 0" at bit 7' of Function 332 byte E is reserved. The "1, 1" code of template 330 creates a flag which is interpreted by the operating system to be the equivalent of "ask user".

It can, therefore, be seen that the Transfer or Measurement templates may be implemented by the user to build a Function without requiring the user to answer many repetitious questions. As Function 332 of FIG. 13 is being built, the operating system looks at each answer in the template 330. If the answer stored at the byte locations of the template is fixed, and valid, that answer is copied and duplicated into the Function as the Function is being built, at a location in the Function which corresponds with the same template location, and the user is never presented with these template answered questions. Those byte locations along the template 330 have invalid answers or which specifically instruct the operating system by flags to "ask the user", must be answered by the user. By having templates as a sub-program within the operating system, the user can create and define templates of his own design, in addition to those transfer and measurement functions supplied by the manufacturer.

As a further example of the preferred embodiment of the structure of a Transfer Function, it will be noted that as Transfer Functions are being built by the operating system, a sub-set of information contained within each Transfer Function is present and known as a "range" (previously defined). The range structure in the preferred embodiment is a 6 byte field within each Transfer (or Measure) Function. The "range" defines, in the Transfer Function, the pattern or manner in which fluid transfer is to occur. For example, one type of "range" performs a transfer by moving from well to well, one row at a time, from a "destination" well to a "destination" ending well. Another type of "range" moves from well to well from a designated starting point up and down the columns to a designated ending point. In a Measure Function, a "range" defines which locations will be measured.

The first byte of the 6 byte "range" field which defines the manner of fluid transfer, in the preferred embodiment, stores, in its first four bits, a number which specifies the source location, namely, the tray locations of any compartments of the table 28 (FIG. 1) or the bulk dispense flask. Bits 4-7 of this first range byte specifies the manner of fluid transfer according to range type, such as a "range" distributing by rows or a "range" distributing by columns, as previously discussed.

The second byte of this "range" structure stores information specifying which row within a microtiter marks the source row. Bits 0-3 are used exclusively to specify a location by row (1-8) for the starting point of a fluid transfer which begins within a microtiter plate 27. If a liquid transfer is to begin from a fluid reservoir resident in one of the compartments of the tray, then bits 4-7 of this second byte define the configuration of the fluid reservoir as a starting location. If the starting point is the well of a microtiter plate, then bits 4-7 are not used and have zeros to hold in place the structure of the second byte.

In a similar manner, the starting column is designated by number from 1-12 by the user and stored in bits 0-4 where the starting "source" position of this Transfer Function is a well of a microtiter plate. The remaining bits of this third byte are not used and merely hold a place as a means of identifying and segregating the information contained in byte 3 to be directed only to the location of the starting column.

Byte four is similar in structure to the second byte in that it identifies the ending row with the range structure on a microtiter plate. This fourth byte would have all zeros if the ending transfer point were other than one of eight rows of a microtiter plate. Byte four may be specially coded to indicate that the end row is the same as the source or the same as the starting position.

The fifth byte provides information on the end position of the column; i.e., that is the location of the last well by column to be filled with fluid, The sixth byte of the range structure provides information to the operating system as to what to do once the range is fully executed. Should the range be repeated? Should the work station stop further movement? Should the operating system "ask the user" to supply information as to what the system should do when the range is completed. Bytes 3-7 of the 6th byte allow the user to repeat the transfer according to one of 29 different manners of liquid transfer preprogrammed within the operating system. When all zeros appear in bits 3-7 of byte 6, the user is asked what action to take. This coding is reserved for use by a template to create a Function. In other words, the template which contains a range structure in byte 6, which codes bits 3-7, with all zeros, flags or indicates to the operating system that when building the Function, the user must be asked if further action is to be taken once the range is executed.

The structure of the generic transfer function makes use of the range structure information, previously discussed, in order to create templates or build Functions. In the preferred embodiment the Transfer Function structure may be 31 bytes long.

The first byte of the 31 byte Transfer Function specifies the particular Function type (transfer, serial dilution, or other previously discussed types), stored as a two-digit hexadecimal number. The operating system maintains a file cataloging the Functions by number, which identifies the Functions as a Transfer Function, or a "tip change" Function or the like. This byte is for Function identification purposes only.

The second byte of the Transfer Function is indicative of the entire length of the Function string. In this manner, the operating system is immediately told how long a data string the Transfer Function will be.

Bytes 3-8, being a six-byte field specify the source "range" as defined by the six byte range structure previously discussed. These bytes define the primary pathway of movement in order to get from the source well or wells to the destination wells.

Likewise, bytes 9-14 specify the destination parameters as stored in the 6-byte wide range field previously discussed. As indicated earlier, in order to transfer fluid from a source to a destination, the operating system needs to know the manner in which the Function is to be executed. The six byte "range" defines the manner of fluid transfer, which information is then used by the transfer functions and stored at bytes 3-8 and 9-14 of the Transfer Function.

Byte 15 is reserved to indicate a "replication size". A "replication" is a method of fluid transfer in which, for example, fluid might be transferred from three source wells to six different destination wells three wells at a time, which the operating system defines as a replication of two. Where no replication is to occur, a zero is stored in this 15th byte.

Byte 16 identifies for the Transfer Function, a particular destination height (352 of FIG. 14) at which a pipette tip or bulk dispense module is to be positioned within a well from which liquid is aspirated or to which liquid is dispensed. The first four bits of the 16th byte (high nybble) indicate the height at the source which the pipette tip or bulk dispense module is to be positioned, while the lower four bits (low nybble) indicate the height position within the source wells where the fluid is to be transferred. A "nybble" is 4 bits long. Two "nybbles" or eight bits make a byte.

The 17th byte of the 31 byte Transfer Function indicates which module (single tip pipettor, bulk dispense module, etc.) is to be selected to perform the fluid transfer.

Bytes 18 and 19 are reserved to store and specify the volume in microliters of liquid which is going to be dispensed to each destination.

The 20th byte provides information concerning the parameter "tip touch"; i.e., whether a pipette tip should touch against the wall of the microtiter well in order to shake the last drops of fluid out of the microtiter tip. The first two bits of this 20th byte are reserved to indicate whether tip touching is to be done at the source, the destination, or both locations, or neither locations (four possible answers, storable within two bits). Additionally, when a template is created, the first two bits may store the message "1-1" which indicates "ask user". Bits 2-4 of the 20th byte are reserved to provide a dispense rate. These three bits (2-4 of byte 20) allow the user to select one of six different rates for dispensing fluid at the destination (since six choices are available for dispense rate, three bits are needed to store the binary equivalents of one through six). Bits 5-7 of the 20th byte are reserved to indicate where within a well the tip touch is to occur (also one of eight choices).

In the preferred embodiment, byte 21 of the Transfer Function is used to provide information for the operating system whether mixing shall occur at the source. The first two bits of the 21st byte answer the question of whether any mixing is to occur. A "mixing cycle" is defined to mean liquid once drawn into the pipette tip and dispensed right back to the well from which the liquid was aspirated. A message of "1-1" stored in these two bits of the template 330 flag the prompt during Function building "ask user". Bits 2-5 are reserved to indicate, when mixing is selected, the number of cycles of mixing desired. The number of mixing cycles available vary from 1-8. The higher the mixing cycle number stored at these bits 2-5 of byte 21, the more times the pipette tip aspirates and dispenses back to the same well to perform a mix. Bits 6-7 of the 21st byte are reserved to indicate at what level within the well the mixing is to occur. If a low level is chosen, the pipette tip is brought to the bottom of the well and stays there throughout the mixing cycle. If the high number choice is selected, the pipette tip is brought to the bottom, begins to draw liquid, moves up from the bottom and then dispenses the liquid. Mixing is useful in preventing premature precipitation of the specimen being studied.

Bytes 22 and 23 are reserved to indicate the amount of volume that is to be dispensed and aspirated during the mixing cycle of byte 21. The 24th byte is of identical structure internally to the byte 21 except it indicates the nature of mixing to occur at the destination wells rather than the source well mixing defined by byte 21. The first two bits of the 24th byte store information as to whether any mixing is to be done; bits 2-5 of byte 24 indicate the number of mixing cycles, and bits 6-7 indicate whether the mix is to be a "low" or a "high" mix, as described earlier with regard to byte 21. The instruction "1-1" stored in bits 6-7 of byte 24 are reserved in the template 330 which corresponds to this Transfer Function 332 (FIG. 13) to flag the prompt "ask user".

Bytes 25 and 26 are reserved for the user to specify the amount or volume of fluid to be mixed at the destination.

The 27th byte asks whether "metronoming" is to be performed. Metronoming is a technique for the dispensing of liquid into destinations. If the metronome rate were set to be five seconds, this would indicate to the operating system that the user wants liquid dispensed into destinations at precise five second intervals. In order to maintain metronoming, the work station will remain idle above destinations until the time designated by the metronoming rate occurs. Bits 2-4 of the 27th byte indicate whether or not an agitation of the microtiter tray 27 by reciprocal movement of the table 28 is to occur and if it is to occur, at what rate. Bits 5- 7 of byte 27 are reserved to select the amplitude of agitation or how sharply and quickly the agitation is to occur.

Bytes 28 and 29 are reserved to indicate the number of seconds between the beats of the metronoming selected by byte 27. Byte 28 and 29 having meaning only where metronoming is selected by the user. If the user does not elect to metronome in byte 27, bytes 28 and 29 are filled with zeros and their places are held to maintain the integrity of the Transfer Function structure.

Byte 30 is reserved to indicate to the operating system whether the user desires a tip change. The first two bits are reserved to determine whether or not a tip change is required. A zero value in bits one and two indicate to the operating system not to change the tips at all. Bits 2-5 indicate the manner of tip changes. The operating system allows user to select various modes of tip change. For example, tip change may occur after each destination has been visited by the pipette tip, after each column has been visited, or after each transfer has been replicated. Bits 6 and 7 of the 30th byte provide data on whether or not the user wishes to prewet the tip. If a 0-0 message is stored in bits 6-7 of byte 30, no prewetting will occur, while a 0-1 indicates prewetting as requested, and a 1-1 is reserved for use by the template 30 to "ask the user".

Byte 31 may be used to inform the user about each individual source to destination move as it occurs in the form of a log. This is useful for analysis in kinetic assays. For example, this byte 31 may be used to inform the user of the optical density characteristics for each well.

The Measure Function structure has many similarities to the Transfer Function byte string structure. However, in one important way the Measure Function structure will change depending upon the nature of the measurement. For example, an optical measurement requires co-ordination of the electro-optical and mechanical components of the optical measurement system. The source of light and fiber optics resides in the central ridge 22 (FIG. 1 and FIG. 3B), while the detection mechanism is resident in a detachable module, as shown in FIGS. 3A and 3B. Optical measurement requires co-ordination of movement of the table 28 with the pod 42 and arm 44 to insure that the light source is aligned with the detection module. Filter selection is required for optical density measurement.

On the other hand, pH measurement does not require filter selection; nor is there any need to position the module above the central ridge 22 for alignment with the optical fiber bundle 24 (FIG. 1). The pH detection system may be entirely housed in a detachable module.

Thus, each Measure Function requires a differently structured sequence of instructional code since the Measure Functions are inherently different. In order to accommodate this inherent difference, the Measure structure requires "breaks" or "branch-off" points so that different types of instructions may be substituted to accommodate the unique measurement undertaken.

The byte field which comprises the Measurement Function begins with a first byte directed at Function identification; e.g., that the Function is a Transfer or Measure Function. This byte identifies, for the operating system, that the Function being built is an "Optical Density Measure Function."

The second byte in the Measure Function is one which tells the opera,ting system how long the byte field is; i.e., how many bytes in the Measure Function.

The third through the eight byte is reserved for the Measure Range and array information; i.e., as previously discussed, these bytes provide information as to the pathway or manner in which wells of a microtiter plate will be read and which wells among the pathway or "range" will form a sub-grouping or array.

The next two bytes identify the type of Measure Function, i.e., optical density rather than pH.

The eleventh byte allows for calibration. The user is queried whether he wishes to calibrate. If he chooses calibration, the entire spectrum of measurement will be set, so that at one end of the measurement scale, a reading will indicate no absorbance, while the other end indicates total absorbance.

The twelfth byte is directed at filter options for optical density. Does the user wish to use a single filter, or two separate filters, one after the other at each measured well, where the final absorbance reading would be the difference between the reading obtained by the first filter and the reading obtained by the second filter. This two-filter option is selected to obtain a form of common mode rejection, where greater absorbance sensitivity is desired.

The thirteenth byte is directed at filter choice. One of four filters in the optical density filter wheel 160 of FIG. 3A is chosen.

The fourteenth and fifteenth bytes of the Measure Function structure are reserved for addressing the issue of "blanking" as applied to optical density readings. In biotechnology, it has heretofore been common that when optical density readings of sample specimen are made, the user has the option of whether he chooses to "blank". By choosing "blanking", the user elects to further refine the absorbance data by taking into account the fact that there is no perfect absorbance or transmission of light through a specimen. That is, even an empty well made from transparent plastic material has some absorbance. When an experimenter wishes to discount the absorbance from such interference, such as the absorbance of an empty microtiter plate well bottom, he may wish to "blank" by removing from the data that portion of absorbance attributable to obstructions, such as the refraction at the bottom of microtiter well, in the optical pathway. Another example of extraneous optical data that a user may wish to remove by blanking might be the absorbance that arises due to the introduction of a chromogene when the user is undertaking to perform an ELISA technique experimentation (ELISA is an enzyme traceable immunoassay). As known in the biological applications art, an ELISA may be performed where chromogenes are used which, in the presence of "tagged" enzymes attached to an antibody or antigen under biological study, reveal themselves by a change in color within the wells when the "tagged" enzyme is present. Blanking may be used to discount some of the absorbance that arises due to the presence of the chromogene by itself in a solution, so that an absorbance reading where a chromogene interacts with an enzyme can be more accurately determined.

Blanking may be performed by allowing the user to input an empirically derived value which is then subtracted from all absorbance data as the experiment progresses. Alternatively, the user may be allowed to read new blanks or to use previously determined blanks as the basis of this absorbance refinement process. The pattern for blanking may be obtained by measuring an entire column or row of blanking solution to determine its absorbance and then subtracting an average value from all experimental data. For some forms of optical density measurement, it may be necessary to provide an extra byte to store additional blanking data.

The sixteenth through the twenty-first bytes define the destination range, which mirrors the structure of the Transfer Function which provides for a destination information range at this point. For optical density readings, this six-byte field need not be used, but its place in the Measure Function structure may be preserved for adaptation and use to specialized optical readings.

The twenty-second byte is reserved for replicate size. In a Transfer Function, this byte is used to literally replicate equal amounts of sample into a given number of sample wells. Within the Measure Function, replicate size is used to read a given number of wells, such as three wells, at a time and post absorbance values which represent an average of every three wells measured. Bytes twenty-three and twenty-four are reserved for the data output options and level types to be read. These two bytes are reserved for determining the manner in which the output of information from the optical readings is to be presented to the user. One option, of course, is a straight absorbance reading; additionally, the user is able to simply perform optical density readings on the basis of whether a given reading for the well being measured is above or below a preset level of absorbance. The format of such data would simply be $(-,+)$. This format would indicate whether each of the wells were above or below a desirable amount of absorbance and would allow the user to more quickly evaluate the data for his limited purpose. Additionally, the user is given the option of having two levels of output, where if the absorbance is below a predetermined level, it is negative; if it is above a predetermined value, it is positive; and if it is double the predetermined value, it is $(++)$. Finally, the user is given still another option to group the data into ten separate groupings or bins where within each bin the data would be $+$ or $-$ that bin level. For example, a $4+$ would be an absorbance reading in a fourth grouping at the higher end of that grouping. Output levels of absorbance can be set based on original calibrations or new levels taken to obtain new levels. The arrays designated in the third through eighth bytes setting range and array values may be used in the twenty-fourth and twenty-fifth bytes of the Measure Function to set the output level based on an array grouping 1 or an output level based on an array grouping 2. That is, output levels might be determined in relation to how our particular well may be read in relation to the members of a preselected array 1 or array 2. An additional byte may be reserved for extra output data and preserved in the Measure structure.

Bytes twenty-six and twenty-seven may be reserved to set the higher output levels and the lower output levels so that threshholds of readings may be set.

Where a blank value is to be stored for use in blanking, that blank value may be stored at the twenty-eighth byte.

Bytes twenty-nine and thirty provide the user the option of measuring a particular pattern of wells defined by the array and reading those patterns according to a menu of selectable types of reading criteria. For example, the user might select that the array defined previously in the third through eighth bytes may be used to define the pattern of measurement, where those wells which are members of the array so defined may be measured with a differing calibration than the wells originally measured. These options allow further refinement of optical measurement data by the user. Another option is data bytes reserved to identify and locate outlier wells. An "outlier" well is one having optical density measurement results well outside established ranges or predictable limits, and therefore usually of limited value in statistical tabulations. Such a byte would allow the user to identify those wells that would otherwise impair the validity of the optical density data.

The thirty-first through thirty-fourth bytes of the Measure Function are reserved for upper measure pattern threshold inputs and lower measure pattern threshold inputs. These bytes which set the upper and lower thresholds of measurements that are made according to an array pattern as discussed with regard to the twenty-ninth and thirtieth bytes.

Bytes thirty-five and thirty-six are reserved to provide information which allows the arrays as used in the twenty-ninth and thirtieth bytes to define a measure pattern, to also be used to set the lower and upper measure pattern limits. An example of such pattern is where an array of wells is used in a predetermined pattern according to an array for the establishment of a spectrum of values for performing optical measurement.

The thirty-seventh byte may be preserved for an internal delay, much like that used in the Transfer Function structure. This internal delay allows measurement to be performed well to well at a predetermined rate. In between well measurements, the user has the option to agitate the samples so as to clear up any turbidity and obtain more precise optical measurements. Bytes thirty-eight and thirty-nine are reserved to store in seconds the amount of time that the user wishes to set as the internal delay factor.

Byte forty is reserved for a logging option whereby the entire Measurement Function may be logged in a time clock and as the data is presented to a screen or print, the time when the information was obtained was also recorded. This logging task is similar to the logging option available in the Transfer Function.

Additionally, more bytes may be added to the Measure structure to provide the user to perform analysis on the data, to perform calculations based on that analysis, and post results on a printed record.

Thus, although the Transfer Function and Measure Function have similarities, such as ranges, internal delay, and logging characteristics, they must by necessity be structured differently because of the different nature of their operation. However, once an array is defined within a Measure Function, it is given a name and may be retrieved during the execution of the Transfer Function so that true feedback can occur. For example, the Measurement Function may define an array of well locations which represent those wells which achieve an optimum optical reading; this same array, the members of which are defined as the Measure Function is run by the operating system, may then be used to select the location of those wells from which subsequent transfers of fluids will be made. In this manner, a predefined hierarchial structure for the Transfer and Measure Functions within the operating system allow feedback operations to occur. Additionally, Measure Functions, like Transfer Functions, are amenable to template creation and the use of templates to create Measure Functions.

As previously discussed, Measure Functions differ in that they have breaks or branch-outs for differing types of measurements. For example, after the calibration byte of the Measure Function, a break might occur before entering the filter option and filter selection, since filters are needed for optical measurements but might not be needed for another type of measurement, such as pH. At this point immediately after the eleventh byte which allows for calibration of an instrument, the Measure Function might have a flag which causes the operating system to follow a different set of data structure relative to pH, when the name of the Function is indicated in the first Function type byte is other than an optical measurement.

The preferred embodiment has selected a particular system of "Methods", "Procedures", and "Functions" to emulate a real-world chemical or biological assay. These designations are arbitrary, and more generally may be conceived of as a convenient means for sequentially loading an ordered set of sequentially arranged instructions into the operating system. What is important to note is that the assay may be carried out during the run sector, if the set of instructions made during the build sector are strung together one at a time, each Function set being retrieved by its name to create an orderly arrangement of operational instructions.

Each Transfer Function is, thus, built to be a 31 byte field. Likewise, Measure Functions have range structures identical to Transfer Functions and for a particular measuring device, are all the same byte field length. In this manner, both Measure Functions and Transfer Functions may be built according to the structure and information provided by a template. By having identical "range" structures, Transfer Functions and Measure Functions are built so that during the "Run" sector of the operating system program, the "range" structure and information of a Measure Function is used by a Transfer Function to transfer specimen from only those wells, (defined in the Measure Function as an "array") within the Measure Function range which have optimum optical characteristics worthy of further examination. Thus, the array of optimum wells with the Measure Function range becomes the array of wells which the Transfer Function is instructed to transfer.

An additional utility is the "editing" utility. The operating system provides the user the ability to edit an entire Procedure, Function by Function. This utility of Editing may be used during the build sector of the operating system by the user to create a set of instructions for conducting a complete experimental assay. The assay is made from a plurality of Methods, each having subsets of Procedures, where Procedures in one Method may be substantially similar, but still different from, Procedures in another Method. Rather than building entirely new Procedures each time a new Method is built, one may store a copy of a Procedure at the time of its initial building, and then "Edit" that Procedure, Function by Function, to create a new Procedure for use later in the same original Method or for another Method. Thus, the "Editing" utility also cuts down the time required for a user to build the complete set of instructions necessary to command and operate the automated laboratory work station of this invention.

In the preferred embodiment, located immediately below the central ridge 22 is an emergency stop bar. This emergency stop bar may be activated to prevent a mishap that might arise at those points during the run or execution sector of the operating system, where the user must directly and physically interact with the laboratory work station. For example, at the beginning of each new Procedure that is created, the user is asked whether or not a change of configuration is desirable. If a change in configuration is desirable, then during the build sector of the operating system, the set of instructions which conduct the new Procedure alert the operating system that the user must reconfigure the component resident on the table 28 of FIG. 1. Should the operating system malfunction and overlook the need for configuration change, the user, during the run sector of the operating system, may activate the emergency stop bar to indicate to the EIU 35 and the computer 39 that it is necessary for the user to physically change the configuration of the table 28. By activating the emergency stop bar, the solenoid is activated in a conventional manner to cause a pawl to lock the rotating arm drive motor 126 (see FIG. 2) house within the elevator tower 46 of FIG. 1, preventing motion of the arm downward of the arm 44 downward along the elevator tower 46 and possibly harming the user during configuration. Additionally, this manually activated emergency signal interrupts the microprocessor within the EIU 35 which in turn indicates to the computer 39 that a display must appear on the computer screen telling the user that the emergency stop bar has been activated. In the preferred embodiment, a light at the top of elevator tower 46 turns off during the emergency stop which indicates to the user that it is safe to move components and reconfigure the table 28.

In the above example cited, if the operating system is properly functioning, when a new Procedure is to be built, a configuration Function is presented to the user by the operating system and the user informs the operating system as to the change of configuration required at the beginning of this Procedure. During the run sector of the operating system, when this new Procedure is reached (as the instructions which control the performance of the overall experimental assay are sequentially executed), the laboratory work station will automatically stop for the predetermined period to enable the user to reconfigure manually the components located on the table 28. During this automatic stop period of the run sector of the operating system, the light at the top of the tower 46 turns "off" indicating that it is safe for the user to reconfigure the table 28. Additionally, a solenoid is energized which controls a locking pawl, in a conventional manner, preventing further rotation of the arm drive motor 126 (FIG. 2) housed within the elevator tower 46 so that the arm 44 will remain in a locked position while the user attempts to reconfigure the table 28.

Additionally, as will be explained in detail later in this application, a series of six byte fields of instructions are built during the run sector of the operating system in order to provide commands to the motors needed to carry out the fluid and measurement transportation functions necessary to operated the automated laboratory work station.

FIG. 15A shows the configuration of the computer hardware used to accomplish motor control in the preferred embodiment. The intelligence which controls the timing of signals to the stepper motors may use the Zilog Z80 microprocessor manufactured by Zilog, Inc. of Cupertino, Calif.

In order to run digitally driven stepper motors, the motor control system must have stored in the memory of the EIU 35 (FIG. 1) the proper ramp and slew tables for each motor. These tables define the motion of each motor according a step motion profile, as illustrated in FIG. 15B. Typically, each motor is "ramped-up" (492) or accelerated up to a desired velocity (490), and "ramped-down" (498) or decelerated to a slower velocity or resting position. The information necessary to properly accelerate or decelerate the stepper motor is contained in the ramp tables which are resident in the computer's memory. The "slew rate" is included between the ramp value sets and defined as velocity to be maintained at a maximum steady value. During the slew phase of motor operation, no acceleration occurs. The "slew rate" is defined as a count or length of time over which the motor will take a single step at a constant angular velocity. Slew count may be derived by the microprocessor from data in the ramp tables and data provided by the user to indicate the total run time for the motor. The "slew count" is the total distance which the motor will move (measured in motor steps) less the sum of the total number of acceleration and deceleration ramp steps. FIG. 15B shows that the motor ramps up (492) at one measurable step (494) at a time, whereby the angular velocity (1) (vertical axis) increases one step 494 at a time. When a desired constant velocity is reached, this "slew" rate is maintained for a fixed number of steps (490) measurable, also, in time or discrete motor steps. After "slew" 490 or constant velocity period ends, "ramp-down" 498 occurs one discrete step (496) at a time. (The horizontal axis measures time in discrete numbers of motor steps.)

The ramp information tables are stacked in the computer memory, and a pointer is set up within the memory which will select values from the table in a software programmed order for use as required by the microprocessor 412.

The microprocessor 412 directs one set of table values at a time to the essential component devices (420, 430, 440, 444) along the data bus lines. The address bus allows the microprocessor 412 to indicate to each of the component devices (namely interrupt controller 420, output port 430, and counters 440 and 444) where the data from memory is located within memory and where within each component the data is to be directed. For example, as the pointer of the memory directs transmission of the first acceleration value from the memory, such data is transmitted to various component devices (420, 430, 440, and 444) along the data bus line, enabling the software to be implemented by the microprocessor 412, according to a preprogrammed formula which the microprocessor 412 applies to the data.

Motor drive information is transferred from memory to the output port 430 over the data bus, one motor drive step at a time. In the preferred embodiment, output port 430 is a programmable peripheral interface device, such as the 8255A chip manufactured by Intel Corporation of Santa Clara, Calif. For each motor, the output port 430 provides at three of its output pins a separate signal for each of three motor drive characteristics. Each motor (by way of a motor controller 450) is provided with a first signal indicative of stepper motor mode (half step or full step), a second signal indicating motor rotational direction (clockwise or counterclockwise direction), and a third signal which opens or closes the "OR" gate 436. Thus, eighteen separate signals would control as many as six different motors. (The five other sets of signals are sent to each of five other motor controllers, like 450.) The "OR" gate 436 controls the flow of stepping signals to the motor controller 450. When the gate 436 is enabled, by the third signal from the output port 430, a fourth signal is sent by the gate 436 to the motor controller 450 which, in turn, causes the stepper motor to advance a single step. When the OR gate 436 is disabled, no drive signal is transmitted to the stepper motor resulting in a motor delay interval. (By definition, an "or" gate is enabled when a low or logic "0" signal is sent to the gate 436 by the output port 430; and, the gate is disabled by a logic high or "1" signal.)

The microprocessor 412, each time it loads a set of motion value into the port 430, also provides a counting number "N" to counters 440 and 444.

In the preferred embodiment, these counters are each one of three counters found within a programmable interval timer, such as the Intel 8253. Counter 440 is programmed as a rate generator or Divide-by-N counter, while counter 444 is programmed to issue an interrupt signal on its terminal count.

Timing for the counter 440 is provided by a 100 KHz signal clock output from frequency divider circuit 416. The divider 416 is synchronized by a 2.5 MHz crystal controlled oscillator 414 which provides the timing to operate the microprocessor 412. When the rate generator counter 440 receives an instruction word from the microprocessor 412, the rate generator proceeds to count input pulses from the divider 416 and produce a single output signal for every N pulses counted, where N is the value of an instruction word which the microprocessor can change, from step to step, changing the time duration between output signals from the counter 440. The duration of the output signal, when input to "OR" gate 436, can control motor speed since the rate at which stepping commands (an instruction output from gate 436 commanding movement of the motor a single step) are sent to the motor controller 450 determines speed. Each stepping command moves the stepper motor one step. The counter 440 determines how often the motor controller 450 will move the stepper motor one step, thus setting the rate of stepping commands which, in turn, controls motor speed. During both acceleration and deceleration, the rate counter 440 counts down. The length of the count determines the length of each deceleration or acceleration step. In this manner, acceleration, for example, occurs because more terminal countdowns of counter 440 are reached per unit time in a sequence of steps. If the motor controller 450 is ordered to step faster, the motor accelerates. The "N" value for each step thereby controls acceleration.

The output signal of counter 440 is also communicated to the clock input of counter 444. When the counter 444 receives a signal from counter 440, it decrements one number of its count. The number of decrements needed for counter 444 to reach zero or terminal count is set by the instruction word stored in memory and sent to the counter 444 by the microprocessor 412 over the data bus. During acceleration ramping up (492) or deceleration (498) down (FIG. 15B), this number is "one". During the slew period 490, this number is the number of slew steps to be taken; or, during motor dwell or delay time, the length of time (measured in steps set by Rate Generator Counter 440) that the motor is to not operate. Alternatively, dwell time is the amount of time that a first motor will remain idle, while a second reference motor runs.

During ramp periods 492 and 498, the stored program performs a separate countdown, decrements for a value "N" stored in memory, keeping track of the number of programmed acceleration and deceleration steps. Each time counter 444 reaches terminal count (zero), the output of timer 444 changes state and signals an interrupt command to the interrupt controller 420. (The interrupt controller 420 is a Universal Interrupt Controller AM 9519A manufactured by Advanced Micro Devices of Sunnyvale, Calif.) Upon receipt of an output signal from the counter 444, the interrupt controller 420 signals the microprocessor causing an interrupt of the microprocessor 412. The microprocessor 412 reacts to the interrupt signal by checking the memory ramp count (acceleration or deceleration). If the ramp count has not yet reached zero, the next ramp instruction word is loaded over the data bus into the counter 440 and a one is loaded into counter 444. The microprocessor then leaves the interrupt routine and returns to its other processing duties.

When the acceleration ramp count reaches zero (0) (after successive loops by the counters, interrupt controller, and the microprocessor through the previously described steps), the processor loads a slew rate into counter 440 and a slew step count into counter 444. These counters proceed to count over the entire slew period (440). The counter 440 sets the clocking or rate of count for the counter 444 as before, but counter 444 only issues an interrupt signal once the slew period is ended. Thus, during constant angular velocity or during motor rest periods, the microprocessor is not interrupted; and, therefore has more time to control other peripherals or otherwise perform its functions. At the end of constant velocity or slew, deceleration begins and an interrupt signal is generated by counter 444 every step of the deceleration ramp 498, in a manner similar to acceleration mode 492 (FIG. 15B). Once the motor completes a ramping cycle and ends a deceleration ramp count, the processor writes a signal to the output port 430 to disable and close gate 436. In this manner, delay arises and may be prolonged for fixed length of time until the counter 444 to decrement to zero, this delay time being set by the microprocessor 412 according to programmed memory-stored instructions. Delays cause the motor to stop movement and become idle; thus, a "delay" is a time period measured according to a discrete number of steps, the time length of each step usually measured according to a reference to the movement of another motor, as previously discussed.

Actual motor control is achieved in a conventional manner by a model L297 controller working in tandem with an L298 controller, both the L297 stepper motor controller and the L298 Bridge Driver being manufactured by SGS-Ates Semiconductor Corp. of Agrate Brianza, Italy. The motor control system herein disclosed provides the necessary signals to allow the motor controller 450 to drive a single motor. To implement the system, six motor controllers are required to run six motors. Motor control may be programmed according to instructions which, in the preferred embodiment, may be presented to the components of the motor control system of FIG. 15A in groups of six byte fields, each field being identical in structure, and each field providing sufficient data to move a first motor according to the movements of a second motor. Movement of the first motor is directed in one discrete movement of a single field. Two fields would be necessary to move a motor in two discrete directions. For example, movement of the pod drive motor 124 (FIG. 2), for moving the pod 42, and the table drive motor 122, for moving the table 28, need to be co-ordinated to move the pod 42 so as to transport fluid from a source well on a microtiter plate diagonally to a new location across the plate; if collision with other implements, such as tips or test tubes in the travel path is to be avoided, one motor must delay while the other one operates. Six motors may be run by the motor control system disclosed; however, the preferred embodiment work station requires presently only five motors to operate.

The structure of each six byte field of software instructions directing motor motion is as follows in the preferred embodiment:

The first byte may identify the motor being moved (first motor), the direction of motor armature rotation, and which of a variety of rates for ramping are to be selected. In the event no specialized rate of acceleration or ramping is selected, a default ramping table is used as the rate of acceleration for this motor. (The various types of ramping rate tables are each stored in a ROM (or a special RAM loaded table is chosen) for selection by the ramp table pointer within the EIU 35 memory).

The second and third bytes of the motor control field store the number of steps necessary to move the first motor. From this data, the microprocessor 412 is able to calculate the total number of steps in the ramp-up sequence 492, the slew period 490, and the ramp-down period 498 (FIG. 15B). Thus, the second and third bytes provide information to operate the motor control hardware components, such as the entire length of time and total steps taken by a single motor driven in a discrete motion.

The fourth and fifth bytes determine the total time (in number of steps of motor two) for which the first motor remains idle or delays while motor two operates. The sixth byte identifies the name of the second motor (one of five motors in the preferred embodiment). The sixth byte may additionally instruct the first motor to delay based upon the rate which the second motor is slewing.

In summary, each six byte field instructs a first motor how to move, at a given rate, and for a given time. Additionally, the field provides information as to how long this first motor may wait or delay, until a second motor reaches a pre-set destination point. running. In this manner the operation of the motors may be coordinated to avoid collisions, since all motors may be coordinated to move with reference to at least one other motor. The string of six byte fields are built during the "run" phase of the operating system. Running of function string information causes the remote computer 39 (FIG. 1) to build an entire string of motor command fields before the motors are actually run. Once the entire string of six byte-wide fields of motor commands are built (based upon "function" instructions interpreted during the "run" phase of the operating system) for a particular function, then the string of fields are executed and run, causing the motors to operate. Because motor motion is undertaken only in accordance with preprogrammed instructions contained in the six byte fields, collision avoidance is built into the operation and running of the motors, because each discrete motion command (a single six byte field) may contain delay information for a first motor with reference to a previously running second motor. (The second motor itself may be delayed based upon the third motor, etc.) This inherent nesting of instructions for motor movement renders collision avoidance a natural product of the coding sequence.

Such a motor control system, as hereinbefore disclosed offers the type of flexible motor control needed to smoothly run the laboratory workstation. The ramps created may be of a wide variety of shape and slope, suited to the loads of each motor separately. The cost of implementing the disclosed design is significantly less than stepper motor controller like the CY512 referred to in the Background of the Invention. Furthermore, the microprocessor can read the motor operating parameters while the motor is running and take appropriate action to achieve the performance of desired motions. (The motor runs above resonance speeds to avoid the inherent problems of resonance in the stepper motor.) The five motors of the workstation may be run independently or co-ordinated for collision avoidance. A big advantage of the disclosed system is the ability to run the motor during slew or delay without interrupting the microprocessor. These flexibilities, when incorporated into the operating system's overall control of the automated workstation, greatly enhance the versatility of use of the laboratory workstation.

It should be noted that the preferred embodiment is only illustrative of one form of a multi-purpose laboratory work station. The scope of the invention is not necessarily limited to the preferred embodiment. Many structural changes are possible and those changes are intended to be within the scope of this disclosure. For example, the interchangeable modules 52 may include a pH probe to measure acidity or a stirring rod to agitate the fluid sample. A video camera may be contained as a module, or be linked by an imaging coherent fiber optic bundle, and may ride the pod 42 or be positioned on top of the ridge 22 to photograph or analyze the image of the experiment on a kinetic basis. The microtiter plates may be substituted by a matrix of test tubes holding samples for an experimental assay. Consequently, the specific structural and functional details of the multi-purpose laboratory work station are merely representative, yet they are deemed to afford the best embodiment for purposes of disclosure and for providing support for the claims which define the scope of the present invention.

What is claimed is:

1. A method of programming a programmable controller comprising the steps of:
    providing a template comprising a statement shell having a plurality of decision windows;
    holding in each decision window one of a plurality of bit patterns representing either a parameter or an instruction to query the user;
    providing a replicate shell comprising a plurality of memory storage locations for holding a plurality of bit patterns;
    examining a first of said bit patterns in said decision windows of said statement shell,
    wherein when said bit pattern represents a parameter, said bit pattern is replicated in said replicate shell, and
    wherein when said bit pattern represents an instruction to query the user, a message is presented to said user to elicit a user parameter for said decision window, the user parameter is interpreted, a bit pattern is provided corresponding to said user parameter, and the bit pattern is replicated corresponding to said user parameter in said replicate shell;
    serially repeating at least said examining step until said plurality of memory storage locations in said replicate shell are filled with bit patterns corresponding to parameters, said filled replicate shell defining at least one executable instruction for said programmable controller; and
    programming said controller with said at least one executable instruction defining a program and executing said program.

2. A method as in claim 1 wherein said examining step comprises comparing said bit pattern to a range of valid patterns to determine whether said bit pattern is valid before replicating said bit pattern in said replicate shell.

3. A method as in claim 1 wherein after a user parameter has been interpreted, said bit pattern corresponding to said user parameter is compared to a range of possible valid user parameter before replicating said bit pattern in said replicate shell.

4. A method as in claim 1 wherein after said bit pattern corresponding to said user parameter has been replicated, the next examining step is directed to a decision window in the template consistent with the user parameter, whereby certain decision windows may be skipped or range of possible valid user parameter may be limited depending on said user parameter replicated.

5. A method as in claim 1 wherein said message is presented in a manner including presenting a plurality of candidate parameters for selection by a user.

* * * * *